United States Patent [19]
Vittori et al.

[11] Patent Number: 5,652,265
[45] Date of Patent: Jul. 29, 1997

[54] PRODUCTION OF RHEIN AND RHEIN DERIVATIVES

[75] Inventors: Natale Vittori, Caracas, Venezuela; Michael Collins, Blue Mounds, Wis.

[73] Assignee: Wisconsin Alumni Research Foundation, Madison, Wis.

[21] Appl. No.: 412,545

[22] Filed: Mar. 29, 1995

[51] Int. Cl.$^6$ ................................................ A61K 31/38
[52] U.S. Cl. ............................................................ 514/548
[58] Field of Search ................................... 514/510, 548

[56] References Cited

U.S. PATENT DOCUMENTS

| | | | |
|---|---|---|---|
| 4,215,062 | 7/1980 | Mitscher | 260/365 |
| 4,346,103 | 8/1982 | Friedmann | 514/548 |
| 5,393,898 | 2/1995 | Carcasona et al. | 552/626 |

FOREIGN PATENT DOCUMENTS

| | | | |
|---|---|---|---|
| A1 2072283 | 12/1992 | Canada. | |
| A1 2090423 | 12/1992 | Canada. | |
| 0 374 890 | 6/1990 | European Pat. Off.. | |

OTHER PUBLICATIONS

W. G. G. Bruce, "Investigations On The Antibacterial Activity In The Aloe," *South African Medical Journal* 41:984 (1967).

R. Y. Gottshall et al., "The Occurrence Of Antibacterial Substances Active Against *Mycobacterium Tuberculosis* In Seed Plants," presented at the Second National Symposium on Recent Advances in Antibiotics Research, Washington, D.C., Apr. 11–12, 1949.

J. M. Watt and M. G. Breyer-Brandwijk, *The Medicinal And Poisonous Plants of Southern And Eastern Africa* (E & S Livingstone LTD, Edinburgh and London, 2nd ed.), pp. 679–80 (1962).

D.L. Barnard et al., "Evaluation Of The Antiviral Activity Of Anthraquinones, Anthrones, And Anthraquinone Derivatives Against Human Cytomegalovirus," *Antiviral Res.* 17(1):63–77 (1992).

W. Wang et al., "Biochemical Study Of Chinese Rhubarb. Inhibition Of Anthraquinone Derivatives On Anaerobic Bacteria," *Zhongguo Yaoke Daxue Xuebao* 21(6): 354–57 (1990).

Z. Chen et al., "Biochemical Study of Chinese Rhubarb. Study On The Antigonococcus Activity Of Anthraquinone Derivatives," *Zhongguo Yaoke Daxue Xuebao* 21(6): 373–74 (1990).

Y. Cai et al., "Biochemical Study Of The Chinese Rhubarb. Comparison Of Biological Activity Of The Metabolites Of Anthraquinone Derivatives In Animal Body," *Zhongguo Yaoke Daxue Xuebao* 19(4): 282–84 (1988).

M. Fanciulli et al., "Inhibition of Membrane Redox Activity By Rhein And Adriamycin In Human Glioma Cells," *Anticancer Drugs* 3(6):615–21 (1992).

A. Floridi et al., "Cytotoxic Effect Of The Association Of BCNU With Rhein or Lonidamine On A Human Glioma Cell Line," *Anticancer Res.* 11(2):789–92 (1991).

S. Castiglione et al., "Rhein Inhibits Glucose Uptake In Ehrlich Ascites Tumor Cells By Alteration Of Membrane-Associated Functions," *Anticancer Drugs* 4(3):407–14 (1993).

S. Castiglione et al., "Inhibition Of Protein Synthesis In Neoplastic Cells By Rhein," *Biochem. Pharmacol.* 40(5):967–73 (1990).

A. Floridi et al., "Effect Of Rhein On The Glucose Metabolism Of Ehrlich Ascites Tumor Cells,"*Biochem. Pharmacol.* 40(2):217–22 (1990).

M. Mian et al., "Rhein: An Anthraquinone That Modulates Superoxide Anion Production From Human Neutrophils," *J. Pharm. and Pharmacol.* 39(10):815–17 (1987).

P. T. Gallagher et al., "A New Synthesis Of Rhein," *Tetrahedron Letters* 35(2):289–92 (1994).

E.H.C. Verhaeren et al., "The Antagonistic Effects Of Morphine On Rhein-Stimulated Fluid, Electrolytes, And Glucose Movements In Guinea-Pig Perfused Colon," *J. Pharm. and Pharmacol.* 39(1):39–44 (1987).

K.E. Malterud et al., "Antioxidant And Radical Scavenging Effects Of Anthraquinones And Anthrones,"(Basel) 47(Supp. 1):77–85 (1993).

K. Tsukida et al., "Studies on the Constituents of Polygonaceous Plants. I. Detection of Hydroxyanthraquinones and its Distribution in Plants," *J. Pharma. Soc. Japan* 74(3):224–29 (1954).

C.S. Shah et al., "Phytochemical Studies of Seeds of *Cassia Tora* L. and *Cassia Occidentalis* L.," *Indian J. Pharm.* 31(1):27–30 (1969).

L. Boross, "Isolation And Identification Of The Antibacterial Substance of *Kniphofia uvaria*," *Acta Chim. Hung.* 35:195–98 (1963).

R.U. Marin, "Estudios Especiales de Investigacion y Valoracion de Derivados Antraquinonicos en Plantas de Chile," *Anal. Fac. Quim. Farm. (Univ. Chile)* 18:19–25 (1966).

J. Schlossberger et al., "Chemische Untersuchung der Rhabarberwurzel," *Ann. Chem., Justus Liebigs* 50:196–223 (1844).

Y. Ohshima et al., "High-Performance Liquid Chromatographic Separation Of Rhubarb Constituents," *J. Chromatogr.* 360(1):303–06 (1986).

G.W. Van Eijk et al., "Separation and Identification Of Naturally Occuring Anthraquinones By Capillary Gas Chromatography and Gas Chromatography Mass Spectometry," *J. Chromatogr.* 295(2):497–502 (1984).

O.A. Oesterle, "Rhein aus Aloë-Emodin," *Arch. Pharm.*, 241:604–07 (1903).

(List continued on next page.)

*Primary Examiner*—John W. Rollins
*Attorney, Agent, or Firm*—Medlen & Carroll, LLP

[57] ABSTRACT

Methods for the production of rhein and rhein derivatives from aloin-containing substances are described. The oxidation of aloe yellow sap to form aloe-emodin is described, as are the further steps used to treat aloe-emodin to form rhein or rhein derivatives. The present invention provides for the production of rhein and rhein derivatives by methods that are more efficient and economical than those used previously.

34 Claims, 9 Drawing Sheets

OTHER PUBLICATIONS

R. Robinson et al., "Experiments on the Constitution of the Aloins. Part I.," J. Chem. Soc. 5:1085–96 (1909).

O. Fischer et al., "IX. Zur Kenntnis der Chrysophansäure, des Frangula–Emodins und einiger Oxoniumverbindungen von Anthracenderivaten," J. Prakt. Chem. 84(2):369–82 (1911).

Ayyanger et al., J. Sci. Ind. Res. (India) 20B:493 (1961).

U.R. Zope et al., "A Short Synthesis Of Diacetyl Rhein," Chem. Ind. (London) 124 (1988).

*The Merck Index*, Eleventh Edition, Susan Budavari, ed., "302, Aloe," Merck & Co., Inc., Rahway, N.J. (1989).

European Pharmacopoeia, vol. 3, "Aloe Barbadensis," pp. 145–47 (1975).

British Pharmacopoeia 1973, "Aloes," pp. 18–19 (1973).

Koch et al., "The Horizontal TLC–Chamber And Its Application To A Rapid Quantitative Determination Of Aloin," PZ (Pharmazeutishche Zeitung) Wissenschaft 137(6):250–53 (1993).

J.C. Sherris, "Mycobacteria," in *Medical Microbiology—An Introduction to Infectious Diseases*, John C. Sherris ed., pp. 291–304, Elsevier Science Publishing Co., Inc., New York, NY (1984).

S.W. Dooley et al., "Multidrug–Resistant Tuberculosis," Ann. Int. Med. 117:257–59 (1992).

J.P. Nadler, "Multidrug–Resistant Tuberculosis," N. Eng. J. Med. 327:1172–75 (1992).

*The Merck Index*, Eleventh Edition, Susan Budavari, ed., "8175. Rhein," Merck & Co., Inc., Rahway, N.J. (1989).

M. Barinaga, "New Test Catches Drug–Resistant TB in the Spotlight," Science 260:750 (1993).

A. Yagi et al., "Antimicrobial Tetrahydroanthraquinones From a Strain of *Alternaria solani*, "Phytochem., 33(1):87–91 (1993).

N.B. Ganguli et al., "Mode of Action of Active Principles From Stem Bark of *Albizzia lebbeck* Benth," Indian J. Exp. Biol., 31(2):125–129 (1993).

H.N. Abramson et al., "Synthesis of Anthraquinonyl Glucosaminosides and Studies on the Influence of Aglycone Hydroxyl Substitution on Superoxide Generation, DNA Binding, and Antimicrobial Properties, " *J. Med. Chem.*, 29(9):1709–1714 (1986).

S. Kitanaka and M. Takido, "Studies on the Constituents in the Roots of *Cassia obtusifolia* L. and the Antimicrobial Activities of the Roots and the Seeds, " Yakugaku Zasshi 106(4):302–306 (1986).

H. Anke et al., "Metalabolic Products of Microorganisms 185. The Anthraquinones of the *Aspergilus glaucus* Group 1. Occurrence, Isolation, Identification and Antimicrobial Activity, " Arch. Microbiol., 126(3):223–230 (1980).

N. Okamura et al., "Altersolanol–Related Antimicrobial Compounds From a Strain of *Alternaria solani*," Phytochem., 34(4):1005–1009 (1993).

T. Ogasawara et al., "Production in High Yield of a Napthoquinone by a Hairy Root Culture of *Sesamum indicum*, " Phytochem., 33(5):1095–1098 (1993).

H. Haraguchi et al., "Action Mode of Antimicrobial Altersolanol A in *Pseudomonas aeruginosa*, " Biosci. Biotechnol. Biochem., 56(8):1221–24 (1992).

I. Messana et al., "An Anthraquinone and Three Napthopyrone Derivatives From *Cassia pudibunda*, " Phythochem., 30(2):708–10 (1991).

T.M. Sarg et al., "Phytochemical and Antimicrobial Investigation of *Hemerocallis fulva* L. Grown in Egypt, " Int. J. Crude Drug Res., 28(2):153–156 (1990).

S.A.Z. Mahmoud et al., "Microbiological Studies on the Phyllosphere of the Desert Plant *Aloe vera* L., " Egyptian J. Microbiol., 21(2):229–238 (1987).

R. Wijnsma et la., "Anthraquinones as Phytoalexins in Cell and Tissue Cultures of *Cinchona* sp., " Plant Cell Rept, 4(5):241–244 (1985).

L. Drobnica et al., "Effect of 2,3–dinitrilo–1,4–dithia–9, 10–anthraquinone on *Mycobacterium smegmatis*," Folia Microbiol., 25(5):403–411 (1980).

C–L. Chen and Q–H. Chen, "Biochemical Study of Chinese Rhubarb. XIX. Localization of Inhibition of Anthraquinone Derivatives on the Mitochondrial Respiratory Chain, " Zhongguo Yaoke Daxue Xuebao 22(1):12–18 (1987).

K. Jahn et al., "Detection of Anthranoids From 'Ganna Ganna' (Cassia species), " Planta Med., 56:562 (1990).

X. Peigen et al., "Ethnopharmacological Study of Chinese Rhubarb, " J. Ethnopharmacol., 10:275–293 (1984).

J. Cudlin et al., "Biological Activity of Hydroxy Anthraquinones and their Glycosides Toward Microorganisms, " Folia Microbiol., 21:54–57 (1975).

J.L. Bloomer et al., "Preparation of Functionalized Juglone Acetates and Juglones via 1,4–Dimethoxynaphthalene Derivatives: Synthesis of Anthraquinones Related to Rhein and Aloe Emodin, " J. Org. Chem. 58:7906–12 (1993).

Rhein

Aloin Isomer A

Aloin Isomer B

|  | R1 | R2 | Configuration |
|---|---|---|---|
| Aloin A | H | H | S,S |
| Aloin B | H | H | R,S |
| Aloinoside A | α–L–rhamnosyl | H | S,S |
| Aloinoside B | α–L–rhamnosyl | H | R,S |
| 5–Hydroxyaloin | H | OH | R,S |

R
H: Aloesin
R: feruloyl : 2"–o–feruloylaloesin

PRODUCTION OF RHEIN AND RHEIN DERIVATIVES

FIELD OF INVENTION

The present invention relates to the production of anthraquinone derivatives for use in the treatment of various medical conditions and particularly to methods for the production of rhein and rhein derivatives from aloe yellow sap.

BACKGROUND OF THE INVENTION

Rhein is an anthraquinone compound that is currently the subject of great interest by the scientific community. Reports of its biological activity are based on both in vitro and in vivo studies. Of the numerous areas of ongoing research, the most notable include the antiviral, antitumor and antioxidant properties of rhein and its derivatives. In addition, past studies have demonstrated rhein's emetic effect on colonic mucosa. Rhein is also the active metabolite of a preparation that has been marketed in Italy since 1986 for the treatment of osteoarthritis.

In terms of rhein's antiviral properties, the bulk of experimentation has been performed with human cytomegalovirus (HCMV). Tests performed on ganciclovir-resistant strains of HCMV suggest that rhein and several other compounds may be useful as prototypes for synthesizing a class of anti-HCMV drugs that are effective against ganciclovir-sensitive and -resistant strains of HCMV. [See Barnard et al. "Evaluation Of The Antiviral Activity Of Anthraquinones, Anthrones, And Anthraquinone Derivatives Against Human Cytomegalovirus," Antiviral Res. 17(1):63–77 (1992)].

Rhein has been shown to have a bacteriostatic effect on some anaerobic bacteria, including *Bacteroides fragilis*. [See Wang et al. "Biochemical Study Of Chinese Rhubarb. Inhibition Of Anthraquinone Derivatives On Anaerobic Bacteria," Zhongguo Yaoke Daxue Xuebao 21(6):354–57 (1990)]. Though not as active as metronidazole, the anthraquinone derivatives have exhibited activity similar to other anti-anaerobic drugs, including cefoxitin. Additional studies have shown activity against *Neisseria gonorrhea* and the gram positive cocci *Staphylococcus aureus* and *Streptococcus viridans*. [See Chen et al. "Biochemical Study Of Chinese Rhubarb. Study On The Antigonococcus Activity Of Anthraquinone Derivatives," Zhongguo Yaoke Daxue Xuebao 21(6):373–74 (1990) and Cai et al. "Biochemical Study Of The Chinese Rhubarb. Comparison Of Biological Activity Of The Metabolites Of Anthraquinone Derivatives," Zhongguo Yaoke Daxue Xuebao 19(4):282–84 (1988)].

Rhein also may become a valuable antitumor agent. Rhein has been combined with adriamycin in in vitro studies involving human glioma cells. [See Fanciulli et al. "Inhibition of Membrane Redox Activity By Rhein And Adriamycin In Human Glioma Cells," Anticancer Drugs 3(6):615–21 (1992)]. A strong synergistic response was observed with this combination, suggesting that rhein may be useful in improving the therapeutic index of adriamycin and in decreasing its toxicity. A similar study has indicated that it may be beneficial to combine rhein and the nitrosurea carmustine (BCNU). [See Floridi et al. "Cytotoxic Effect Of The Association Of BCNU With Rhein Or Lonidamine On A Human Glioma Cell Line," Anticancer Res. 11(2):789–92 (1991)]. Several mechanisms of antitumor activity have been attributed to rhein. Rhein is known to inhibit glucose uptake by neoplastic cells, and studies have demonstrated that it inhibits aerobic and anaerobic glycolysis. Rhein has also been shown to impair protein synthesis of neoplastic cells through a decrease in amino acid incorporation. [See Castiglione et al. "Rhein Inhibits Glucose Uptake In Ehrlich Ascites Tumor Cells By Alteration Of Membrane-Associated Functions," Anticancer Drugs 4(3):407–14 (1993); Castiglione et al. "Inhibition Of Protein Synthesis In Neoplastic Cells By Rhein," Biochem. Pharmacol. 40(5):967–73 (1990); and Floridi et al. "Effect Of Rhein On The Glucose Metabolism Of Ehrlich Ascites Tumor Cells," Biochem. Pharmacol. 40(2):217–22 (1990)].

Several other studies have investigated the antioxidant, antiarthritic and antirheumatic, and laxative effects of rhein and its derivatives. Of note, much research has been directed at the long-term treatment of osteoarthritis using rhein, and rhein is the active metabolite of a preparation marketed in Italy for treating that malady. [See generally Mian et al. "Rheim An Anthraquinone That Modulates Superoxide Anion Production From Human Neutrophils," J. Pharm. and Pharmacol. 39(10):815–17 (1987); Gallaher et al. "A New Synthesis Of Rhein," Tetrahedron Letters 35(2):289–92 (1994); Verhaeren et al. "The Antagonistic Effects Of Morphine On Rhein-Stimulated Fluid, Electrolytes, And Glucose Movements In Guinea-Pig Perfused Colon," J. Pharm. and Pharmacol. 39(1):39–44 (1987); and Malterud et al. "Antioxidant And Radical Scavenging Effects Of Anthraquinones And Anthrones," Pharmacol. (Basel) 47(Supp. 1):77–85 (1993)].

Chemically speaking, Rhein is the common name that describes the anthraquinone present in rhubarb (Rhei rhizoma). (FIG. 1) Rhein possesses the following chemical and non-chemical names: 9,10-dihydro-4,5-dihydroxy-9,10-dioxo-2-anthracenecarboxylic acid; 1,8-dihydroxyanthraquinone-3-carboxylic acid; 4,5-dihydroxyanthraquinone-2-carboxylic acid; chrysazin-3-carboxylic acid; monorhein; rheic acid; cassic acid; parietic acid; and rhubarb yellow. Numerous methods have been undertaken to produce rhein, and the methods can be grouped into the two broad categories of extraction and purification from plant tissue and chemical modification of other substrates.

Effort has been expended over the years improving the techniques of extracting and purifying rhein and various other oxyanthraquinones from plant tissue. In nature, Rhein can be found in a number of different plant species, and in many species it occurs both free and as a glycoside. These plant species include the roots of Rheum species, Rumex species (Polygonaceae), and *Muehlenbeckia hastulata* (J.S.N.) Stand.es. Macbr. (Polygonaceae), the areal parts of Cassia species (Leguminosae), and the seeds of *Knipholia aloides* (Compositae). [See, e.g., Tsukida et al., J. Pharma. Soc. Japan 74:224–29 (1954); Shah et al. Indian J. Pharm. 31(1):27–30 (1969); Boross, Acta Chim Acad. Sci. Hung. 35:195–98 (1963); Marin, Anal. Fac. Quire. Farm. (Univ. Chile) 18:19 (1966)]. Rhein production by extraction and purification from plant tissue was first reported in 1844 by Schossberger et al., who isolated rhein from Chinese rhubarb. [See Ann. Chem., Justus Licbigs 50:214 (1844)]. However, several major limitations impaired the usefulness of Schossberger et al.'s method, including the presence of Rhein in plant species in only small concentrations and the need for complex separation procedures to isolate it from other similar anthraquinone compounds such as aloe-emodin, eraodin, physcion and chrysophanol; these same limitations have had an adverse impact on subsequent techniques as well. The development of high pressure liquid chromatography (HPLC) has been followed by the publication of several new analytical chemical procedures for the separation of naturally occurring anthraquinones and their associated glycosides. Of special note in this area is the work of Oshima et al., "High-Performance Liquid Chromatographic Separation Of Rhubarb Constituents," J. Chromatogr. 360(1):303–06 (1986), where the anthraquinones and glycosides of rhubarb were simultaneously separated by HPLC on a dimethylamino-bonded silica gel column using a gradient solvent system. In addition, Van Eijk et al., "Separation and Identification Of Naturally Occurring Anthraquinones By Capillary Gas Chromatography and Gas Chromatography Mass Spectometry," J. Chromatogr. 295(2):497–502 (1984), have separated and identified naturally occurring anthraquinones by capillary gas chromatography and gas chromatography mass spectrometry. Other techniques have also been employed to separate and analyze naturally occurring anthraquinone derivatives. Unfortunately, these newer techniques did not overcome the inherent limitations of using extraction and purification as a viable means of producing rhein on a large industrial scale.

The second major category of methods for the production of rhein involves chemical processes performed on various starting substrates. Initial work in this area is attributable to Oesterle, Arch. Pharm., 241:604–07 (1903), who set out to confirm the difference between the rhein obtained by the oxidation of aloe-emodin and the rhein obtained by extraction from the Chinese rhubarb. Oesterle oxidized aloe-emodin directly to rhein. He did not obtain a yield greater than 10%; in addition, his product contained eraodin and other oxidized material that can only be removed from the rhein by using a long and tedious crystallization process. Early experimentation was also performed by Robinson et al., J. Chem. Soc. 95:1085–96 (1909), and Fischer et al., J. Prakt. Chem. 84(2):372 (1911), who reported production of rhein and diacetyl rhein by chemical processes that act upon the initial, naturally occurring substrates of aloin and chrysophanic acid. Besides obtaining poor yields, their processes required the presence of both starting substrates in highly pure states, which could only be achieved by laborious and expensive isolation procedures.

Furthermore, scientists' attempts to chemically synthesize the aloin and chrysophanic acid substrates initially met with little success. In regards to aloin, all efforts to chemically synthesize the carbon-carbon linkage between the anthraquinone moiety and the glucose moiety have been unsuccessful. As for chrysophanic acid, several attempts have successfully produced it by chemical synthesis. One attempt of note was that published by Ayyanger et al., J. Sci. Ind. Res. (India) 20B:493–97 (1961). Unfortunately, the chemical scheme utilized by Ayyanger et al., which starts with 1-amino-5-chloro-anthraquinone, is plagued by poor yields and costly starting substances.

Subsequent to the work of Ayyanger et al., supra, most efforts to produce rhein and diacetyl rhein involved chemical procedures that did not involve the use or formation of aloin or chrysophanic acid. Instead, these efforts focused on chemical syntheses utilizing different substrates and chemical manipulations. One such effort occurred in 1988, when Zope et al., "A Short Synthesis Of Diacerhein," Chem. Ind. (London) 124 (1988), published a chemical synthesis scheme for production of diacetyl rhein and rhein. The process utilized by Zope et al. is a retrosynthesis process based on the assumption that the 1-methoxy-3-methyl-8-hydroxy-9,10-anthraquinone could be easily converted into diacetyl rhein. While this unique process, which incorporates a regiselective Diels-Alder reaction to synthesize the 1-methoxy-3-methyl-8-hydroxy-9,10-anthraquinone, was successful, it too resulted in low yields and required expensive materials. In 1994, Gallagher et al., supra, developed a novel procedure for the synthesis of rhein and diacetyl rhein which began with the readily available, albeit very expensive, 1,5-dihydroxynaphthalene. The organic synthesis involves bismethylation of the phenols, followed by a mono-deprotection and carbamate formation. Thereafter, stereospecific oleofination of the naphthaldehyde using the novel phosphonate $(EtO_2)P(O)CH$ $(CO_2Et)$ $CH_2CO_2CBu$ was performed, followed by cyclation of the acid to yield the anthracene product. Though effective, the process involves a series of complex organic reactions that require expensive catalysts. Furthermore, the yield of rhein was only about 6%. Carcasona et al, German Patents DE 4120989 and DE 4120990, have also developed a noteworthy chemical process for the production of rhein and diacetyl rhein. The process involves the reduction of a sennoside mixture, followed by solvent extraction, oxidation of the extract, and finally cleavage of the glucose moiety and acetylation of the rhein. Because the Carcasona process requires extraction of sermosides from the senna plant, the process resembles the first category of processes requiring extraction from natural sources, discussed supra. Though the process's theoretical yield is claimed to be 75% and the final product is claimed to have less than 20 ppm. of aloe-emodin as an impurity, the process has several important drawbacks. First, the process entails a large number of chemical operations and considerable volumes of chemical reactants. Second, special care must be taken with the liquid-liquid partitioning process, which produces an aqueous phase containing diacetyl rhein and an organic phase containing aloe-emodin triacetate. Finally, because the sennosides are extracted from the senna plant which is only found abroad, most notably in India and Egypt, the process entails the cost of importing and processing the starting material even before chemical manipulation can begin.

Clearly, the methods that have been developed thus far to produce rhein are of limited usefulness because of their low yields and/or high cost. A more efficient and economical process is needed to fulfill the larger demand for rhein that is almost certain to develop in the future.

SUMMARY OF THE INVENTION

The present invention relates to the production of anthraquinone derivatives for use in the treatment of various medical conditions and particularly to methods for the production of rhein and rhein derivatives from aloe yellow sap.

The present invention contemplates a method for the production of rhein comprising: a) providing a substance containing aloin; b) oxidizing the aloin-containing substance to form aloe-emodin by use of a ferric salt solution; and c) treating the aloe-emodin to form rhein.

In some embodiments, the aloin-containing substance is a plant exudate. When the aloin-containing substance is a plant exudate, the plant exudate is aloe yellow sap in some embodiments. The aloe yellow sap is obtained from Aloe barbadensis miller in still other embodiments. Different formulations of aloe yellow sap may be used, including aloe stone.

The present invention contemplates several processes for the oxidation of the aloin contained in aloe yellow sap, or different formulations thereof, into aloe-emodin. Each of the preferred processes for the production of aloe-emodin begins with the principle that both aloin isomers A and B present in various formulations of aloe yellow sap can be oxidized to aloe-emodin; there is no need to first isolate aloin isomer A in pure solid form. The present invention contemplates the oxidation of aloin to aloe-emodin with an efficiency of greater than approximately 70%.

In one embodiment of the method for the production of rhein, the oxidation of aloin into aloe-emodin further comprises the steps of: a) adding the aloin to a solution comprising an acid catalyst to create a first reaction mixture; b) reacting the first reaction mixture to produce a dissolution mixture comprising a liquid and a sediment; c) separating the liquid from the sediment by filtering the dissolution mixture to produce a filtrate; d) adding a ferric salt solution and a diluent to the filtrate to create a second reaction mixture; e) reacting the second reaction mixture to produce a reaction product; and f) extracting aloe-emodin from the reaction product.

In the oxidation of aloin to aloe-emodin, the present invention contemplates some embodiments wherein a hydrochloric acid solution is used as an acid catalyst when the ferric salt is ferric chloride. In other embodiments, a sulfuric acid solution is used as an acid catalyst when the ferric salt solution is ferric sulfate.

The present invention contemplates reacting of the second reaction mixture of the aforementioned oxidation procedure in several manners that are dependent on the ferric salt used. In some embodiments where ferric chloride oxidation is performed, the reacting of the second reaction mixture comprises refluxing the second reaction mixture. In other embodiments, the reacting of the second reaction mixture occurs in the presence of ultraviolet irradiation; in still other embodiments, the ultraviolet irradiation comprises leaving the second reaction mixture at room temperature under direct sunlight exposure for a period of time ranging from 5 to 8 days. In some embodiments where ferric sulfate oxidation is performed, the reacting of the second reaction mixture comprises subjecting the mixture to a temperature of greater than 100° C., and preferably approximately 120° to 125° C., and a pressure of greater than 10 psi, and preferably approximately 15 psi.

Additionally, the present invention contemplates the use of ferric salt solutions containing a ferric salt having a proportion, on a gram basis, of ferric ion to ferric salt of between approximately 21 and 23%.

Furthermore, the present invention contemplates the oxidation of aloin to aloe-emodin wherein the extracting of aloe-emodin comprises adding toluene to the reaction product.

The present invention also contemplates several chemical schemes for the production of rhein or rhein derivatives from the aloe-emodin. Each of the schemes entails the same steps of a) acetylating the aloe-emodin to produce aloe-emodin triacetate; b) oxidizing the aloe-emodin triacetate to produce diacetyl rhein; and c) deacetylating the diacetyl rhein to produce rhein. However, the embodiments differ as to whether each of the intermediary compounds is isolated and purified.

One embodiment involves the isolation and purification of each of the intermediary chemical compounds in the production of rhein; specifically, the embodiment involves the isolation and purification of aloe-emodin triacetate and diacetyl rhein in distinct chemical steps prior to the formation of rhein. In other embodiments, diacetyl rhein or rhein are formed directly from aloe-emodin; as such, these embodiments generally are more efficient, and thus less costly, because fewer chemical manipulations are required.

The present invention contemplates the acetylation of aloe-emodin to aloe-emodin triacetate by a) combining aloe-emodin with an acetylating agent and a catalyst to form a reaction mixture; b) reacting the reaction mixture to produce a reaction product; and c) isolating aloe-emodin triacetate from the reaction product.

In some embodiments, the catalyst that is combined with the aloe-emodin is sodium acetate; when sodium acetate is used as the catalyst, in some embodiments the gram-to-gram ratio of the aloe-emodin to sodium acetate is approximately 3:1. In other embodiments, the catalyst that is combined with the aloe-emodin is sulfuric acid; when sulfuric acid is used as the catalyst, in some embodiments the gram-to-gram ratio of the aloe-emodin to the sulfuric acid is approximately 40:1.

Moreover, after the production of diacetyl rhein, the present invention contemplates deacetylating the diacetyl rhein to produce rhein by a) agitating a mixture comprising diacetyl rhein and an alcohol to form a first solution; b) adding a deacetylating agent to the first solution to form a second solution; c) reacting the second solution to form a final solution; and d) isolating rhein from the final solution. In some embodiments, the deacetylating agent comprises potassium hydroxide.

Furthermore, the present invention contemplates producing rhein from aloin-containing substances comprising the steps of: a) providing a substance containing aloin; b) oxidizing the aloin to produce aloe-emodin wherein the oxidizing comprises using a ratio, on a gram basis, of aloin to a ferric salt of between approximately 1:5 and 1:15, and preferably 1:7 and 1:11; and c) treating the aloe-emodin to produce rhein wherein the treating step comprises: (i) acetylating the aloe-emodin to produce aloe-emodin triacetate; (ii) oxidizing the aloe-emodin triacetate to produce diacetyl rhein; and (iii) deacetylating the diacetyl rhein to produce rhein. In some embodiments, the aloin-containing substance is a plant exudate. When the aloin-containing substance is a plant exudate, the plant exudate is aloe yellow sap in some embodiments. The aloe yellow sap is obtained from *Aloe barbadensis miller* in still other embodiments. In some embodiments of the present invention, the ferric salt is ferric chloride, while in other embodiments it is ferric sulfate.

The present invention also contemplates several methods for the production of aloe stone, a concentrated form of aloe yellow sap that may be used in the production of rhein and other anthraquinone derivatives, comprising the steps of: a) providing aloe yellow sap; b) adding an acid and an antioxidant to the aloe yellow sap to form a mixture; and c) heating the mixture to form aloe stone.

In some embodiments of the production of aloe stone, the acid is selected from the group consisting of ascorbic acid, citric acid, malonic acid, maleic acid, pyruvic acid, and phosphoric acid.

In some embodiments of the production of aloe stone, the antioxidant is butylated hydroxytoluene. In other embodiments, the antioxidant is n-propyl gallate.

Additionally, the present invention contemplates a method of treating a mycobacterial infection comprising administering an effective amount of a therapeutic composition of an anthraquinone derivative to a host suspected of suffering from a mycobacterial infection.

In some embodiments of the method of treating a mycobacterial infection, the anthraquinone derivative is selected from the group consisting of rhein, diacetyl rhein, aloe-emodin triacetate, and aloe-emodin.

In other embodiments, the present invention contemplates treating a mycobacterial infection wherein the infection is caused by mycobacteria from the group consisting of *Mycobacterium tuberculosis*, *M. avium*, and *M. paratuberculosis*.

In still other embodiments, the host is selected from the group consisting of humans and animals. When the host is an animal, the present invention contemplates selecting the animal from the group consisting of ruminants, fowl, and swine.

DEFINITIONS

To facilitate understanding of the invention and the chemical schemes set forth in the disclosure that follows, a number of terms are defined below.

The term "substance" refers to a chemically synthesized or naturally derived material, including a plant exudate.

The term "plant exudate" refers to a fluid that passes gradually out of the body of a plant.

The term "aloe yellow sap" refers to the exudate, a yellow viscous liquid, that drains from the basal portion of leaves removed from plants of the genus Aloe (family Liliaceae). Aloe yellow sap is also known as "aloe vera juice".

The term "frangula" refers to the bark of *Rhamnus frangula* (family Rhamnacea).

The term "aloe stone" refers to the concentrated, solid form of aloe yellow sap that is currently commercially available. Aloe stone is generally produced by boiling the aloe yellow sap in large vats exposed to the atmosphere until a thick, viscous liquid is produced. The content of aloin therein usually ranges from 20 to 30% depending on the source of aloe used and the duration and mode of heating.

The term "aloin" refers to a substance present in some Aloe species and made up of aloe-emodin anthrone covalently bonded to a glucose moiety. As depicted in FIG. 2, aloin is composed of two isomers, aloin isomer A and aloin isomer B, defined by the position of the glucose moiety in relationship to aloe-emodin anthrone. Aloin's most common chemical name is 10-glucopyranosyl-1,8-dihydroxy-3-(hydroxymethyl)-9(10H)-anthracenone. Other chemical names employed in the art include 1,8-dihydroxy-3-hydroxymethyl-10-(6-hydroxymethyl-3,4,5-trihydroxy-2-pyranyl)anthrone and 10-(1',5'-anhydroglucosyl)-aloe-emodin-9-anthrone.

The term "aloe-emodin" refers to an intermediate product formed during the processes of the present invention. Aloe-emodin possesses the following chemical names: 1,8-dihydroxy-3-(hydroxymethyl)-9,10-anthracenedione; 1,8-dihydroxy-3-(hydroxymethyl)-anthraquinone; and 3-hydroxymethylchrysazin.

The term "aloe-emodin triacetate" refers to an intermediate product formed during the processes of the present invention. Aloe-emodin triacetate possesses the following chemical names: 1,8 Bis(acetoxy)-3-acetoxymethyl-9,10-anthracenedione.

The term "diacetyl rhein" refers to either an intermediate product or a final product formed during the processes of the present invention. Diacetyl rhein possesses the following chemical names: 4,5-Bis(acetoxy)-9,10-dihydro-9,10-dioxo-2-anthracene carboxylic acid; 9,10-dihydro-4,5-dihydroxy-9,10-dioxo-2-antroic acid diacetate; 1,8-diacetoxy-3-carboxyanthraquinone.

The term "anthraquinone derivative" refers to a polynuclear hydrocarbon characterized by containing the anthraquinone nucleus, $C_{14}H_8O_2$. Another name for the anthraquinone nucleus is 9,10-dioxoanthracene.

The term "rhein" refers to an anthraquinone derivative that is formed during the processes of the present invention. Based on its molecular structure, rhein possesses the following chemical names: 9,10-dihydro-4,5-dihydroxy-9,10-dioxo-2-anthracenecarboxylic acid; 1,8-dihydroxyanthraquinone-3-carboxylic acid; 4,5-dihydroxyanthraquinone-2-carboxylic acid; chrysazin-3-carboxylic acid.

The term "solution" refers to a liquid mixture.

The term "mixture" refers to a mingling together of two or more substances without the occurrence of a reaction by which they would lose their individual properties.

The term "dissolution mixture" refers to a mixture in which all or a portion of a solid substance has been solubilized.

The term "liquid" refers to a freely flowing substance, like water, that is neither solid nor gaseous.

The term "boiling" refers to the heating of a liquid until bubbles of vapor are generated.

The term "agitating" refers to the act of shaking or otherwise moving with a rapid motion.

The term "sediment" refers to an insoluble material that sinks to the bottom of a liquid.

The term "filtrate" refers to the liquid that has passed through a filter.

The term "evaporating" refers to the loss of volume of a liquid by conversion into vapor.

The term "ultraviolet irradiation" refers to electromagnetic rays beyond the violet end of the visible spectrum and typically having wavelengths between 200 and 400 nm.

The term "extraction" refers to the general chemical process of partitioning a material into a solvent, thereby allowing separation and purification of the material.

The term "extracting agent" refers to a solvent into which a material partitions.

The terms "decant" and "decantation" refer to the process of pouring off the upper liquid portion of a fluid containing both a liquid and a sediment, thereby leaving the sediment in the vessel.

The term "oxidation" refers to the general chemical process of combining a molecule with oxygen.

The term "antioxidant" refers to an agent that inhibits oxidation.

The term "acetylating" refers to the general chemical process of adding an acetyl group, $CH_3CO-$, to a molecule, thus forming the acetyl derivative of that molecule.

The term "acetylating agent" refers to a molecule or molecules that can provide an acetyl group, $CH_3CO-$, to another molecule during an acetylation reaction.

The term "deacetylating" refers to the general chemical process of removing an acetyl group, $CH_3CO-$, from a molecule, thus forming the deacetylated derivative of that molecule.

The term "deacetylating agent" refers to a chemical compound that promotes the removal of an acetyl group, $CH_3CO-$, from a molecule.

The term "refluxing" refers to the general chemical process of conducting a reaction at the boiling point of a solution. The process proceeds without loss of vapor due to the presence of a condenser that returns the vapor as a liquid back into the reaction solution.

The term "effective amount" refers to that amount of an anthraquinone derivative that is required to successfully perform a particular function, such as treatment of a mycobacterial infection. The effective amount of an anthraquinone derivative may depend on a number of factors, including the type of mycobacterium involved, the severity of the mycobacterial infection, the immune status of the individual, and the weight of the individual. By way of example, an anthraquinone derivative may be administered in a solid pharmaceutical composition containing between 10 mg and 300 mg of the anthraquinone derivative.

The term "therapeutic composition" refers to a composition that includes an anthraquinone derivative in a pharmaceutically acceptable form. The characteristics of the form will depend on a number of factors, including the mode of administration. For example, a composition for oral administration must be formulated such that the anthraquinone derivative is pharmacologically active following absorption from the gastrointestinal tract. The therapeutic composition may contain diluents, adjuvants and excipients, among other things.

The term "host" refers to humans and animals, including, but not limited to, ruminants, fowl, and swine.

The term "approximately" refers to the actual value being within a range of the indicated value. In general, the actual value will be between 5% (plus or minus) of the indicated value.

DESCRIPTION OF THE INVENTION

The present invention relates to the production of anthraquinone derivatives for use in the treatment of various medical conditions and particularly to methods for the production of rhein and rhein derivatives from aloe yellow sap.

The description of the invention is divided into four parts: I) The Characteristics of Aloe Yellow Sap; II) Analysis Of Aloe Yellow Sap; and III) New Methods For The Production Of Rhein And Rhein Derivatives; and IV) New Uses For Rhein.

I. THE CHARACTERISTICS OF ALOE YELLOW SAP

Figure 1:
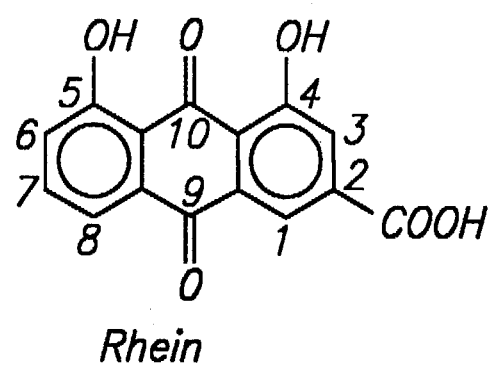
FIG. 1 depicts the chemical structure of rhein, the anthraquinone compound that is synthesized according to the chemical processes of the present invention.
Figure 2:
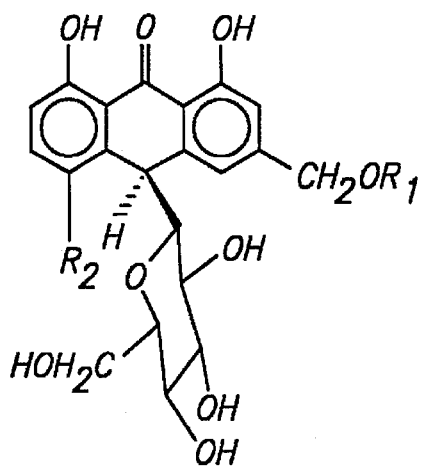
FIG. 2 depicts the molecular structure of the most important compounds present in aloe yellow sap, a starting substrate for the chemical processes of the present invention.
Figure 2:
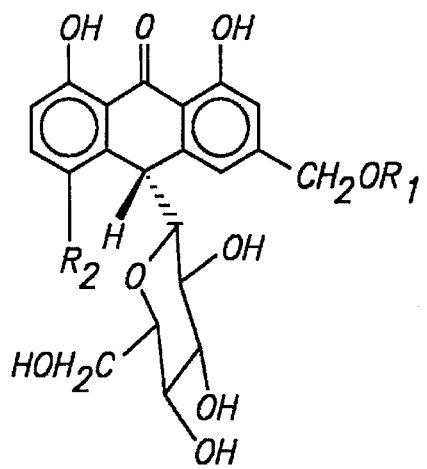
Figure 2:
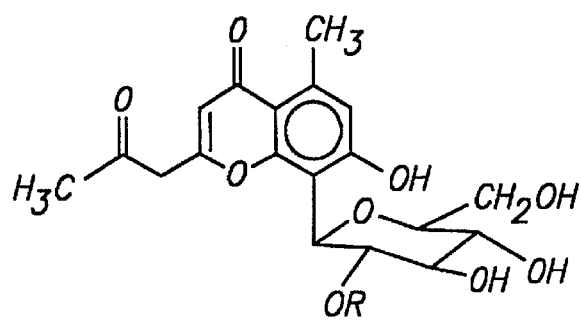
Figure 3:
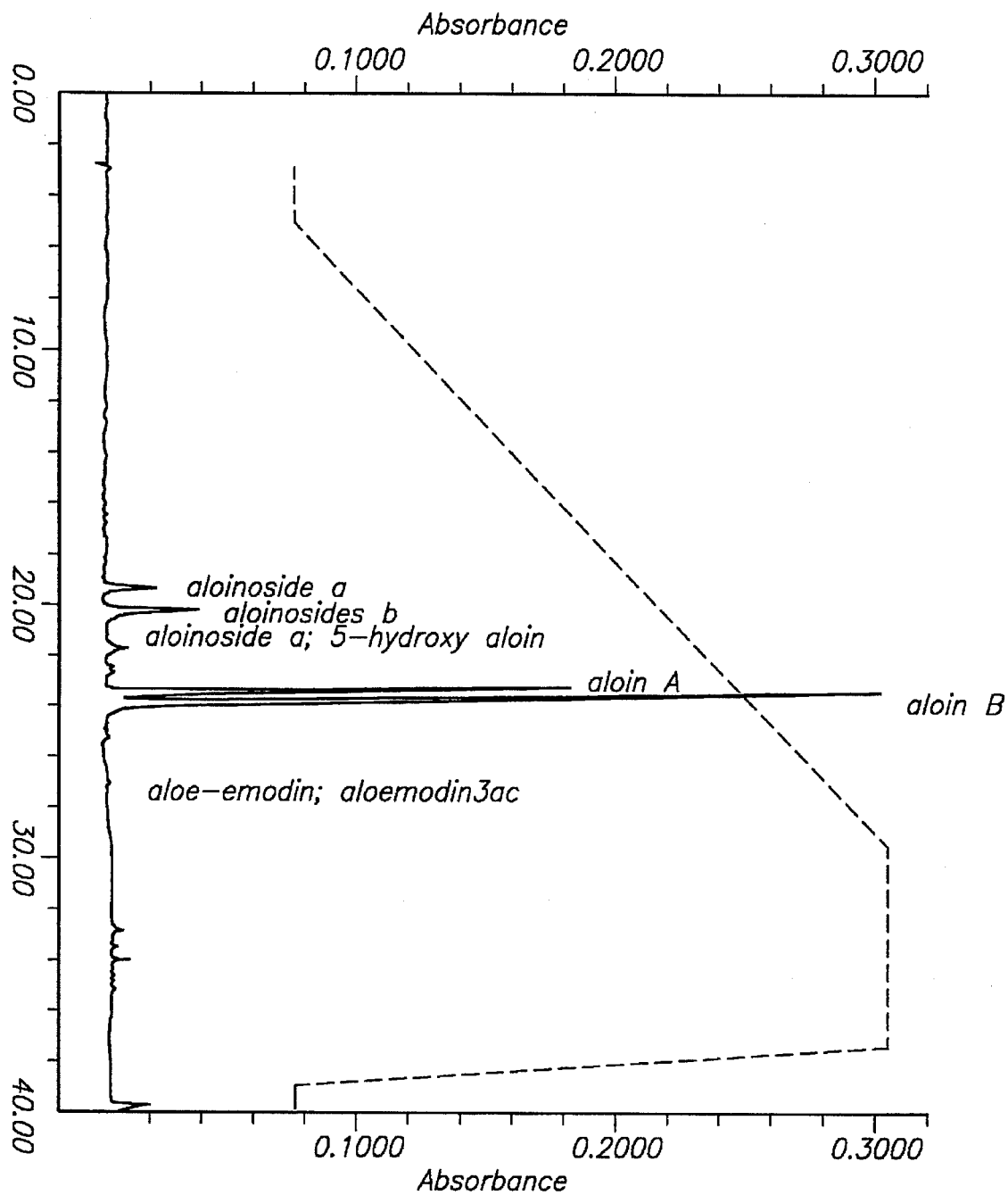
FIG. 3 depicts an HPLC chromatogram of aloe yellow sap. The chromatogram presents the peaks of the compound normally present in aloe yellow sap.

The preferred starting point for the present invention is aloe yellow sap. Aloe yellow sap is a yellow viscous liquid that drains from the basal portion of the aloe leaves after they are removed from the mother plant. Aloe yellow sap is a mixture of several different anthraquinone and aglycone substances, including aloin isomers A and B, aloinoside isomers A and B, 5-hydroxyaloin, and aloesin. (FIG. 2 and FIG. 3). The concentration of each of these chemical substances depends on the plant species and various environmental factors, such as the amount of sunlight the plant receives and the pH of the soil in which it grows.

The rationale for using aloe yellow sap for the production of rhein and diacetyl rhein is the high concentration of aloin present in several aloe plant species. In general, active compounds are found in plant tissues on the order of 0.1 to 1.0%. For example, in the chemical process of Carcasona et al., discussed supra, the sennosides used in the process are found in the senna leaves only in concentrations ranging from about 0.5% to 1.5%. The yield of rhein or diacetyl rhein is obviously limited when the chemical process depends on starting substrates present in such low concentrations. In the case of aloe yellow sap derived from Aloe Barbadensis miller, the concentration of aloin averages, by contrast, from 4% to 6% (w/w), and this value may be even greater depending on the way that the plant is grown.

While aloe yellow sap contains high concentrations of aloin, several reasons explain why aloe yellow sap has not received much attention in the past. First, aloe yellow sap contains products similar to rhein that will also be oxidized in the oxidation process, resulting in contaminates in the final preparation that are difficult to remove. Second, the aloin in aloe yellow sap must be oxidized into the intermediary compound aloe-emodin; this transformation process is difficult to achieve because the carbon-carbon linkage between the anthraquinone and glucose moieties is very resistant to acid hydrolysis, even at high temperatures.

Aloe yellow sap is currently a waste product of the American aloe industry from the process used to make aloe vera gel. Aloe vera gel is produced form the inner parenchyma of the aloe leaf and must be devoid of aloe yellow sap. During the production of the aloe vera gel, the aloe leaves are cut from the mother plant at the leaves' base, and the aloe yellow sap is allowed to drain therefrom over a period of about 10 to 20 minutes. However, some additional aloe yellow sap is still retained in the inner gel and must be removed. Therefore, after the inner gel is homogenized and filtered, the resulting homogenate is pumped through charcoal columns that absorb the aloe yellow sap (and the anthraquinone compounds contained within it). Thereafter, the aloe industry considers the tons of aloe yellow sap that remain absorbed to the charcoal columns to be a waste product. Of economic importance, the aloe yellow sap has recently been obtainable in the United States, Venezuela, and some of the Caribbean islands for an average cost of $5–7 United States Dollars per kilogram; special contractual agreements between a buyer and a seller might make the cost significantly less.

Aloe yellow sap obtained from the aloe leaves contains a very high water content, usually exceeding 80% of the sap by weight. Because a great deal of the aloe yellow sap is produced in Africa and South America and transported elsewhere, it is usually made into a concentrated form to increase its ease of handling. The concentration process involves evaporating the water from the aloe yellow sap in heating tanks, which creates a black viscous material, followed by cooling of the viscous material, which causes it to solidify. The final solid material is referred to as "aloe stone." The preferred methods of the present invention for the production of rhein and rhein derivatives generally start from this aloe stone.

Plants from the same Aloe species may have widely differing contents of aloe yellow sap depending on the conditions under which they are grown. For example, aloe plants grown in California and Texas are irrigated and fertilized to enhance the production of the aloe inner gel; as a result, there is a lower quantity of aloe yellow sap present in the plants' leaves. Conversely, aloe plants grown in certain desert or desert-like regions, such as some areas of Venezuela, Mexico, or Costa Rica, are cultivated solely for the production of aloe yellow sap. In these regions, the plants are not irrigated; rather, the leaves of the plants are induced to absorb the moisture present in the highly humid air. This method of growing the aloe plants results in a higher amount of aloe yellow sap in the plants' leaves. Therefore, aloe yellow sap or aloe stone grown under these conditions of solar incidence and water are most preferred if the aloe yellow sap will be employed for the production of rhein according to the present invention.

The German chemist Alexa describes (EP,A,0,374,890) the production of anthraquinones and anthrones such as aloe-emodin, aloin, and franguline from natural sources, including aloe stone and frangula extracts. However, Alexa did not produce rhein using aloe stone or aloe extracts as starting substrates; in fact, Alexa's chemical scheme was devoted to producing substances for use in the cosmetic industry and to combat various skin-related disorders, such as psoriasis. Importantly, Alexa claims a 50% conversion of aloin to aloe-emodin, while the invention set forth herein contemplates a conversion process with an efficiency of 70% or more.

II. ANALYSIS OF ALOE YELLOW SAP

A. Thin-Layer Chromatography Studies

Thin-layer chromatography has been used by the inventors and others to compare the content and composition of aloe yellow sap in several distinct Aloe species. The inventors have found that Aloe barbadensis miller grown under optimum conditions (see below) has the highest concentration of aloin. Though Aloe barbadensis miller is cultivated in several regions within Venezuela, the inventors preferred samples obtained from the southern region because of its optimum growing conditions. Prior to sampling or chemical testing, the aloe samples taken from that region were cultivated in Venezuela for six years under optimum conditions. Optimum conditions entail arid soil, high solar incidence, and climates characterized by low humidity during the day and high humidity during the night. Of course, the invention does not require that the aloe be specially cultivated. The inventors have compared the yellow sap from aloe plants of Venezuela with that of commercial yellow sap obtained from *Aloe capensis* from Africa.

The TLC plates were developed in the usual manner using a solvent system comprised of ethyl acetate-methanol-water in a ratio of 100:13.5:10. The bands produced were visualized using 5% ethanolic potassium hydroxide, and photographs of the final result plate (not shown) were taken using different filters to assist in observation of the bands. Measurement and quantification of the aloin content of commercially available samples of aloe stone revealed 28-29% (w/w) aloin for the *Aloe barbadensis miller* grown in Venezuela and 12-13% (w/w) aloin for the *Aloe capensis* from Africa; these values reflect the content of aloin in aloe stone, not in fresh aloe yellow sap. It should also be noted that The Merck Index has reported the aloin content in aloe stone derived from *Aloe capensis* as being even less, on the order of 4.5-9%.

B. High Pressure Liquid Chromatography Studies

The inventors also utilized HPLC to analyze the concentration of aloin in Venezuelan yellow sap samples of Aloe barbadensis miller. The HPLC studies were performed using a Beckman System Gold, equipped with a 164 variable wavelength detector. The column used was a Lichrosorb RP-18, C-18 reverse phase (4.6 mm.×250 mm.) made by Alltech Associates, Inc. The tests were performed with the equipment at room temperature. The conditions were as follows: flow at 1.33 ml/min., from 25% methanol in water having A as water and B as methanol. A linear gradient of 25 to 100% of B was used over a period of 25 minutes. Hold it 10 minutes at 100% of B and return to 25% of B. The HPLC "run" was then stopped and the data collected. The results were analyzed using Beckman System Gold software, version 8.1. Unless otherwise indicated, all of the HPLC runs were performed with the detector set at a wavelength of 360 nm.

An aloin standard curve was developed in order to allow determination of the aloin content in samples of aloe yellow sap and aloe stone. The first step in the derivation of the standard curve involved determination of the actual purity of "pure" aloin isomer A. This step was conducted by comparing the aloin content of the experimental samples used with a standard sample of aloin isomer A (purity exceeding 98%) obtained from Sigma Chemical Company; the HPLC chromatogram (not shown) indicated an actual purity for the experimental samples of 98.73% when compared to the standard. Next, standard samples of aloin isomer A of increasing size were run. Standard Sample A contained 60.4 ng and gave a peak area of 1.995; Standard Sample B contained 604 ng and gave a peak area of 13.93; and Standard Sample C contained 3020 ng and gave a peak area of 71.16. Regression analysis of peak area versus concentration of aloin isomer A gave a linear standard curve with slope=0.0235 ($r^2$=0.9999, where $r^2$=the correlation coefficient squared). Aloin concentrations were measured from this standard curve in subsequent experiments.

Following establishment of the aloin standard curve, determination of the aloin content in several samples of Venezuelan Aloe barbadensis miller was carried out. Each HPLC run was performed by dissolving the sample in DMSO and injecting it into the Beckman equipment in a 20 µl loop. After the peak area for each sample was obtained from an HPLC chromatogram (not shown), the total amount of aloin in each sample was calculated. The following calculation, involving data from a sample of aloe stone, serves as a useful example:

(1) Total amount of the sample injected:

=concentration of the sample injected×volume contained in the loop

=290 ng/µl×20

=5800 ng or 5.8 µg (2) Amount of aloin isomer A:

=peak area÷slope of the aloin standard curve

=21.08÷0.0235

=897 ng or 0.897 µg (3) Percentage of aloin isomer A:

=(amount of aloin isomer A÷total mount of sample injected)×100

=(0.897 µg÷5.8 µg)×100

=15.6%

(4) Amount of aloin isomer B:

=peak area÷slope of the aloin standard curve

=21.37÷0.0235

=909 ng or 0.909 µg (5) Percentage of aloin isomer B:

=(amount of aloin isomer B÷total amount of sample injected)×100

=(0.909 µg÷5.8 µg)×100

=15.7%

(6) Total amount of aloin in the sample=15.6%+15.7%= 31.3%.

This example illustrates that by growing *Aloe barbadensis miller* under optimum conditions (low humidity during the day and high humidity at night, high incidence of sun, and arid soil), one may obtain aloin contents exceeding the average range of 20 to 25% normally present in aloe stone. In fact, HPLC analysis has revealed that aloe stone from Venezuelan *Aloe barbadensis miller* may have an aloin content of up to 34.8%. This percentage could then be compared with the percentage of aloin in samples of aloe stone, infra, in order to ascertain how much aloin remained in the aloe stone during its formation from aloe yellow sap.

Data from the samples was obtained with the detector set at a wavelength of 360 nm. At that setting, the chromatograms of aloe yellow sap did not show any peaks of greater than 24 minutes retention, but a chromatogram of aloe stone, the concentrated formulation, did show other peaks. Those other peaks represent substances that are condensation products formed during the process of manufacturing the commercial aloe stone from the aloe yellow sap.

Aloe yellow sap also contains compounds besides aloins which absorb light in the ultraviolet region. In order to detect those compounds, several HPLC runs with samples of Aloe barbadensis miller were performed with the detector set at a wavelength of 254 nm. The resulting chromatograms revealed a number of other peaks, such as those of the aloinosides and aloesin, that are much more pronounced at 254 nm. Furthermore, it should be noted that when a sample of aloe yellow sap was run at a wavelength of 360 nm, no other compounds were present to the right of the peaks representing aloin isomers A and B; however, other compounds were detected to the right of the aloin peaks with the detector set at a wavelength of 254 nm.

III. NEW METHODS FOR THE PRODUCTION OF RHEIN AND RHEIN DERIVATIVES

The present invention contemplates the oxidation of aloe yellow sap or aloe stone into aloe-emodin, which is then transformed into diacetyl rhein or rhein. The preferred process begins with the principle that both aloin isomers A and B present in dried commercial aloe yellow sap can be oxidized to aloe-emodin; there is no need to first isolate aloin isomer A in pure solid form. Several methods are set forth for carrying out this oxidation procedure. Thereafter, several chemical pathways are proposed in order to produce rhein or derivatives thereof.

Prior to performing the initial oxidation of aloin to aloe-emodin, a source of aloin must be obtained. As previously described, aloe stone may be used as the initial substrate because of its ease of handling compared to unmodified aloe yellow sap. Obviously, if more aloin can be retained during the transformation of aloe yellow sap into aloe stone, the potential yield of rhein or rhein derivatives will be higher. TLC and HPLC studies demonstrated that the content of aloin in aloe stone derived from *Aloe Barbadensis miller* varies from 29% to 34%. This variance can be attributed to the source from which aloes are derived and the primitive conditions under which the Venezuelan farmers prepare the aloe stone.

The present invention contemplates several processes that allow the original aloe yellow sap to be transformed into commercial aloe stone without significant loss of aloin. In addition, the processes help prevent the production of oxidation byproducts like aloe resins. The presence of aloe resins leads to the formation of undesirable substances when aloe-emodin is formed; these undesirable substances must be removed by recrystallization, which decreases the yield of aloe-emodin. In general, the process is characterized by the addition of an acid and an antioxidant to the aloe yellow sap prior to evaporation, by heating, of the water contained therein. The acid can be selected from the group comprising ascorbic acid, citric acid, malonic acid, maleic acid, pyruvic acid, and phosphoric acid. BHT, n-propyl gallate, or similar agent can serve as the antioxidant. Examples 1 through 4 set forth in the Experimental section, infra, serve to further illustrate these processes.

It is not intended that the present invention be limited to the situation where special processes are used to obtain aloe stone with a high aloin content. Indeed, commercially available samples of aloe stone may be used as a starting substrate. When a commercially available sample was used, HPLC analysis revealed an aloin content of 28.2%; when compared to the 34.8% obtained from a cultivated sample, this sample contained about 81% of the potential aloin content ((28.2+34.8)×100=81.0%). Furthermore, it is not intended that the present invention be limited to the use of aloe stone as the starting substrate; other forms of aloe yellow sap may also be used. However, it is important to note that when aloe stone is produced from aloe yellow sap, small amounts of aloe-emodin are produced. Thus, aloe stone already contains aloe-emodin, whereas some other sources of aloin do not.

The aloe stone formed from aloe yellow sap is then oxidized to form aloe-emodin. The present invention contemplates the oxidation of aloe yellow sap by a procedure that utilizes a ferric salt solution and an acid catalyst in a manner that optimizes the yield of aloe-emodin. The ferric salt solution may be, for example, ferric chloride or ferric sulfate; regardless of which ferric salt is used, the optimum proportion of iron to the ferric salt compound as a whole (i.e., the hydrated compound) is about 21–23% (on a gram basis). The ferric salts are preferable to stronger oxidizing agents, such as potassium permanganate, hydrogen peroxide, chromium trioxide, and sodium dichromate, because the ferric ion of the ferric salt is the oxidizing agent; the ferric ion is a milder oxidizing agent that does not result in the destruction of the anthraquinone nucleus, as do the stronger oxidizing agents. During the oxidation reaction, the ferric ion is reduced to the ferrous form, presenting the advantage that the anion of the ferric salt (chloride or sulfate) does not participate in the reaction.

The oxidation procedure has been performed using a ferric chloride solution and a HCl catalyst to increase the yield of aloe-emodin. A kinetic study was performed in order to determine the optimum amount of ferric chloride to carry out the oxidation procedure from a given amount of aloin. Ideal conditions existed when pure aloin was combined with $FeCl_3 \cdot 6H_2O$, on a gram basis, in amounts based approximately on the following ratio: 1:10. (See Example 11, infra.) Furthermore, the invention contemplates suitable ratios of reactants ranging from about 1:7 to about 1:11; there is no improvement if higher ratios are used, while the oxidation of aloin is incomplete if lower ratios are used. The use of a specified amount of HCl both disrupts the aloe material when it is being solubilized and ensures that the proper pH exists for maximizing the oxidation. (See Example 5, infra.)

The present invention contemplates two methods for the oxidation of aloin to aloe-emodin using a ferric chloride solution. The first uses a reflux procedure of approximately 8 hours duration to drive the reaction. This procedure avoids the prolonged 24 hour heating process employed in other chemical schemes. The second method was devised in order to reduce the costs associated with the first oxidation procedure. The process takes advantage of the fact that aloin, along with other chemical compounds present in aloe yellow sap, strongly absorbs light in the ultraviolet region of the spectrum. Thus, by allowing the aloe yellow sap to stand in direct sunlight, the aloin therein will be oxidized to aloe-emodin. Of course, other sources of ultraviolet irradiation may be used. If sunlight is used, this second process is carried out at room temperature over a period of about 5 to 8 days; thereafter, a 4 hour reflux procedure is employed to ensure that the oxidation reaction has gone to completion. At the completion of both of the oxidation methods, the product is removed and the aloe-emodin is extracted from it over 8 hours with toluene.

As indicated above, the present invention contemplates the oxidation of aloin to aloe-emodin by use of a ferric salt solution. Oxidation of aloin by a ferric salt solution has been previously described in the literature. For example, the European and the British Pharmacopoeias teach a method of assaying aloes that utilizes a ferric chloride oxidation procedure. [See European Pharmacopoeia, Vol. 3, pp. 145–47 (1975); British Pharmacopoeia 1973, pp. 18–19 (1973)]. More specifically, the Pharmacopoeias' methods were established in order to determine the content of substances in commercial samples of aloe stone that can be transformed into general hydroxyanthraquinones. The hydroxyanthraquinones that are formed by the oxidation procedure, which include aloe-emodin and other compounds, are then extracted by the use of carbon tetrachloride, a solvent, from the reaction mixture. The final extraction solution is then treated with an aqueous solution of sodium hydroxide to form the sodic salt of each of the hydroxyanthraquinones; these compounds are responsible for the red color of the reaction mixture that permits their quantification based on color intensity.

There are several important differences between the methods proposed by the Pharmacopoeias and the methods presented herein. First, the Pharmacopoeias do not mention the use of aloe yellow sap as the starting substrate for the reaction. While the present invention may begin with commercial samples of aloe stone, it may also use fresh aloe yellow sap as the starting substrate for the initial oxidation reaction. Second, the method of the present invention does not use methanol to assist in dissolution of the aloes. Third, the ratio of aloin to ferric chloride (about 1:7 to 1:11) in the present invention differs greatly from that of the Pharmacopoeis, and the inventors have found that their amounts optimize the reaction and thus the yield of aloe-emodin. More specifically, the Pharmacopoeias contemplate a ratio, on a gram basis, of aloin to ferric chloride of about 1:1000; a comparison of the ratios is set forth in detail in Example 11, infra. Next, the conditions of the oxidation reactions themselves are quite different. One of the methods of the present invention is driven by ultraviolet irradiation, a method not described elsewhere, while the other uses an 8 hour reflux procedure. These procedures have been found to eliminate many of the side reactions, incomplete hydroxylation, and uncontrolled oxidation that occurs with other methods. [See, e.g., Koch et al. "The Horizontal TLC-Chamber And Its Application To A Rapid Quantitative Determination Of Aloin," PZ (Pharmazeutishche Zeitung) Wissenschaft 137(6):250–53 (1993)]. Finally, the method of extraction in the present invention also differs. While the Pharmacopoeias describe the use of carbon tetrachloride to extract the aloe-emodin, the method of the present invention extracts the aloe-emodin using an extraction procedure of approximately 8 hours duration that employs toluene; the use of toluene allows aloe-emodin to be selectively extracted, whereas carbon tetrachloride extracts all of the hydroxyanthraquinones. Thus, the method of oxidation of aloin to aloe-emodin contemplated by the present invention is unique.

The efficiency of the method of the present invention that involves an 8 hour ferric chloride oxidation procedure was determined to be 88.3%; that is, 88.3% of the theoretical 100% yield of aloe-emodin was achieved. For the procedure that is driven by ultraviolet irradiation, a yield of about 81% was obtained. As alluded to earlier, Alexa has employed an oxidation procedure for the production of aloe-emodin from aloe yellow sap. However, Alexa described only a 50% conversion using his process. Alexa's chemical process entails numerous features that distinguish it from the processes set forth herein and account for its decreased yield. First, Alexa uses aloe plants of the genus Cape and Curacao, which only yield aloin in the range of 4 to 9%. The present invention uses aloe stone derived from *Aloe barbadensis miller*, which yields aloin in the range of 24 to 34%. Second, the method set forth herein, but not the method proposed by Alexa, contemplates the production of aloe stone without significant loss of aloin or production of oxidation by-products like aloe resins. Third, Alexa's oxidation scheme involves, among other steps, dissolving the aloe extract in solvents like methanol or isopropanol, using an intense four-week oxidation period, and recuperating the aloe-emodin by in situ addition of toluene. Each of these steps ultimately reduces the final yield of aloe-emodin. Though Alexa suggests the use of resins such as Amberlite XAD-7 in the solvent dissolution step, which allows formation of a highly pure product, this too decreases the yield. Conversely, the present invention not only avoids using the aforementioned steps, it also uses a mixture of ferric chloride and HCl solutions in defined amounts, set forth supra and in Example 5, that serves to optimize the oxidation procedure.

Though most experimentation regarding the oxidation procedure has been performed using a ferric chloride solution and a HCl catalyst, the procedure has also been performed using a ferric sulfate solution and a $H_2SO_4$ catalyst. In fact, the use of ferric sulfate under defined conditions, set forth below and in Example 9, to increase the yield of aloe-emodin may be more advantageous than the use of ferric chloride. One of the most significant advantages of using ferric sulfate and $H_2SO_4$ is a small increase in the yield of aloe-emodin. The efficiency of the oxidation using ferric sulfate was determined to be 90.5%. When compared to the 88.3% efficiency of the oxidation method that uses ferric chloride with an 8 hour reflux procedure, the reaction with ferric sulfate is more efficient. The increase may be very appreciable on a larger, industrial scale.

The use of ferric sulfate and $H_2SO_4$ provides other advantages besides the potential of obtaining a higher yield. The first advantage is related to the commercial samples of aloe stone generally used as the starting substrate for the production of aloe-emodin. These samples contain water insoluble substances. Even after the addition of an acidic solution and heating of the resulting mixture, these substances create a solid mass, gummy in texture, that sticks to the walls of the container. Furthermore, the gummy mass of undissolved material obstructs the filtration paper during the filtration step, thus retarding the filtration velocity and decreasing the overall efficiency of the process. The use of $H_2SO_4$ rather than HCl minimizes, to a greater extent, the aforementioned problems that result from the insoluble substances. Second, the reaction between ferric sulfate and aloin occurs much more rapidly (about two hours) than that between ferric chloride and aloin because the reaction can occur at a higher temperature (approximately 125° C.). The reaction using ferric chloride cannot be performed at a temperature of 125° C. because the ferric chloride will generate gaseous vapors of HCl; these vapors will oxidize the autoclave container in which the reaction occurs and are also highly toxic, thus being difficult and dangerous to handle.

A kinetic study, similar to that conducted for the ferric chloride reaction, was performed in order to determine the optimum amount of ferric sulfate to carry out the oxidation procedure from a given amount of aloin. Ideal conditions exist when pure aloin was combined with $Fe_2(SO_4)_3 \cdot 5H_2O$, on a gram basis, in amounts based approximately on the following ratio: 1:10. (See Example 11, infra.) Furthermore, the invention contemplates suitable ratios of reactants ranging from about 1:7 to about 1:11; there is no improvement if higher ratios are used, while the oxidation of aloin is incomplete if lower ratios are used. The addition of the specified amount of $H_2SO_4$ serves both to disrupt the aloe material when it is being solubilized and to ensure that the proper pH exists for maximizing the oxidation. (See Example 9, infra.)

After aloe-emodin has been formed, several procedures may be employed to produce rhein or diacetyl rhein according to the present invention. The details of these procedures are provided in Examples 5 through 8 set forth in the Experimental section, infra. One procedure of the present invention involves three additional steps in which each step entails the isolation and purification of a product. First, the aloe-emodin is acetylated with acetic anhydride and sodium acetate to produce aloe-emodin triacetate; alternatively, sulfuric acid may be used instead of sodium acetate. The aloe-emodin triacetate is then oxidized with chromium trioxide to form diacetyl rhein. Finally, the diacetyl rhein is deacetylated using KOH and water to form rhein.

A second procedure of the present invention resembles the first in that it starts with aloe-emodin and ultimately produces rhein. However, the procedure is more direct in that it does not involve isolation and purification of either aloe-emodin triacetate or diacetyl rhein. Instead, this procedure begins with aloe-emodin and uses an uninterrupted series of chemical steps to produce rhein. The use of this abbreviated procedure increases the efficiency of the chemical scheme, while simultaneously decreasing its cost. However, the chemical steps are similar to those used in the first procedure; that is, aloe-emodin is acetylated to aloe-emodin triacetate, which in turn is oxidized to diacetyl rhein, which is then deacetylated to form rhein.

Another abbreviated procedure of the present invention allows the production of diacetyl rhein from aloe-emodin. In addition to rhein, diacetyl rhein has shown therapeutic activity as an antimycobacterial agent. This procedure is similar to the second process because it bypasses the isolation and purification of aloe-emodin triacetate. However, the series of chemical steps in the second process is terminated following formation of diacetyl rhein in a crude form. That crude form is subsequently purified, yielding the final diacetyl rhein product.

For the first process contemplated by the present invention that began with aloe stone and produced rhein, with aloe-emodin, aloeoemodin triacetate, and diacetyl rhein as intermediates, both HPLC and NMR studies were performed on each of the chemical compounds. (See the Experimental section, Example 5, infra). These studies allowed determination and verification of the purity of each of these chemical compounds. The HPLC studies involved the same equipment and procedures previously set forth. Proton NMR analysis was performed using a Bruker 1H, NMR (Proton) with a frequency of 400 MHz. NMR spectra for aloin, aloe-emodin, aloe-emodin triacetate, diacetyl rhein, and rhein, are set forth in FIGS. 5 through 9.

Finally, it should be pointed out that the HPLC chromatograms and corresponding printouts generated revealed very high purities for rhein and the intermediary chemical compounds, with peak areas generally exceeding 99%. However, one must remember that a peak area of, for example, 100%, does not mean that a compound is 100% pure. The actual purity of each chemical compound is less than that indicated by the chromatographic data, though not less than 95%, because of integration of noise peaks in order to make the chromatograms clearer and sharper. As a result, the purities of each of the chemical compounds will be designated as exceeding 95%; more definitive analysis would reveal a higher purity but would not be fruitful since 95% purity already represents analytical grade for chemical compounds. Due to the high purity of rhein and each chemical intermediate, it is thus unnecessary to correct for purity when calculating the yield following each step.

IV. NEW USES FOR RHEIN

The present invention contemplates the use of rhein in the treatment of mycobacterial infections. Mycobacteria are aerobic organisms that include numerous species pathogenic for both humans and animals. [See generally, Sherris, "Mycobacteria," in Medical Microbiology—An Introduction to Infectious Diseases, John C. Sherris ed., pp. 291–304, Elsevier Science Publishing Co., Inc., New York, N.Y. (1984)]. Mycobacteria have a unique cell wall that has a very high lipid content, creating a hydrophobic cell surface. This unique cell wall not only inhibits the permeability of nutrients into the cells, causing the mycobacteria to have a relatively slow growth rate, it also impairs the effectiveness of treatment with antibiotics.

*Mycobacterium tuberculosis*, the organism responsible for tuberculosis, is one species of mycobacteria that is presently of great concern to humans. It is resistant to many antibiotics currently available, and treatment often requires combinations of three or more drugs for periods exceeding one year. [See Dooly et al. "Multidrug-resistant tuberculosis," Ann. Int. Med. 117:257–59 (1992); Nadler "Multidrug resistant tuberculosis," N. Eng. J. Med. 327:1172–75 (1992)]. The continuing development of drug-resistant organisms, as well as the seriousness of mycobacterial infections in immunosuppressed individuals, confirms the need for additional pharmaceutical agents to treat these infections.

The present invention also contemplates the use of rhein to combat other infections caused by mycobacteria, including veterinary infections. In vitro studies have shown rhein's effectiveness against *M. avium* and *M. paratuberculosis*, both of which may be pathogenic. *M. paratuberculosis* causes an often fatal enteritis in sheep, cattle, and other ruminants (Johne's disease); it has also been associated with Crohn's disease in humans. *M. avium* causes tuberculosis in swine as well as in chickens, pigeons and other birds; in humans, it causes complications in immunocompromised patients.

The present invention contemplates using therapeutic compositions of rhein. It is not intended that the present invention be limited by the particular nature of the therapeutic preparation. For example, such compositions can be provided together with physiologically tolerable liquid (e.g. saline), gel or solid carriers, diluents, adjuvants and excipients, such as pharmaceutical grades of mannitol, lactose, starch, magnesium stearate, sodium saccharin, cellulose, magnesium carbonate, and the like. These compositions typically contain 1%–95% of active ingredient, preferably 2%–70%.

As noted above, these therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

With respect to the mode of administration, the rhein formulations may be investigated for oral, intravenous, intramuscular, intrathecal or topical (including topical ophthalmic) administration.

The rhein formulations contemplated by the present invention may be mixed with diluents or excipients which are physiologically tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

While rhein was found to be the most effective of the anthraquinone derivatives for the treatment of mycobacteria, the intermediate products formed during the chemical production of rhein also exhibited in vitro effectiveness. Specifically, in vitro tests of aloe-emodin, aloe-emodin triacetate, and diacetyl rhein all revealed antimycobacterial activity. For example, tube dilution tests revealed that aloe-emodin's minimum inhibitory concentration against *M. tuberculosis* was at a dilution of 1:100,000; aloe-emodin's antimycobacterial activity was significantly greater than that observed with analogous tests of aloin isomer A, in which the minimum inhibitory concentration was at a dilution of 1:8000.

The present invention contemplates that doses for treatment of mycobacterial infections are in the range of those contemplated for the treatment of multiple sclerosis. U.S. Pat. No. 4,346,103 (the '103 patent) to Friedmann (hereby incorporated by reference) contemplates solid pharmaceutical compositions (i.e., capsules, tablets, or suppositories) containing 10 mg to 300 mg of an anthraquinone derivative. The preferable daily dose for humans is contemplated to be between 25 mg and 500 mg. By comparison, daily doses between 0.40 mg/kg and 10 mg/kg are contemplated for the administration to animals. Due to the growth characteristics of mycobacteria (presented above) and because of the resistance of mycobacteria, especially *Mycobacterium tuberculosis*, to many drugs, it is contemplated that the duration of treatment with the anthraquinone derivatives will be comparable to that of currently available antimycobacterial agents. Thus, treatment of at least six to nine months is contemplated, as is the use of the anthraquinone derivatives in combination with other antibiotics. Of course, other dosing regimens are within the scope of the present invention.

EXPERIMENTAL

In the disclosure which follows, the following abbreviations apply: μl (microliters); ml (milliliters); g (grams); mg (milligrams); μg (micrograms); ng (nanograms); cm (centimeters); mm (millimeters); nm (nanometers); °C. (degrees Centigrade); MW (molecular weight); N (normal); ppm. (parts per million); MHz. (Megahertz); w/w (weight-to-weight); min. (minutes); No. (number); psi (pounds per square inch); NMR (nuclear magnetic resonance); $^1$H-NMR (proton nuclear magnetic resonance spectra); HPLC (high pressure liquid chromatography); TLC (thin-layer chromatography); Alltech (Alltech Associates, Inc., Deerfield, Ill.); Beckman (Beckman Instruments, San Ramon, Calif.); Bruker (Bruker Instruments, Fremont, Calif.); Sigma (Sigma Chemical Company, St. Louis, Mo.); DMSO (dimethyl sulfoxide); DMSO-$d_6$ [deuterated dimethyl sulfoxide; (dimethyl sulfoxide)-$d_6$]; CD$_3$OD (deuterated methyl alcohol; methyl-$d_3$ alcohol-d); CDCl$_3$ (deuterated chloroform, chloroform-d); HCl (hydrochloric acid); H$_2$SO$_4$ (sulfuric acid); KOH (potassium hydroxide); H$_2$O (water); HCl-H$_2$O (aqueous solution of hydrochloric acid); FeCl$_3$·6H$_2$O (ferric chloride, hexahydrate; iron [III] chloride, hexahydrate); Fe$_2$(SO$_4$)$_3$·5H$_2$O (ferric sulfate, pentahydrate; iron [III] sulfate, pentahydrate); BHT (butylated hydroxytoluene; 2,6-Di-tert-butyl-4-methylphenol; 2,6-Di-tert-butyl-p-cresol); n-propyl-gallate (3,4,5-trihydroxybenzoic acid, n-propylester).

The following examples serve to illustrate certain preferred embodiments and aspects of the present invention and are not to be construed as limiting the scope thereof. The experimental disclosure which follows is divided into: I) Processes For The Preparation Of Aloe Stone; II) Processes For The Production Of Rhein And Rhein Derivatives; and III) Other Examples.

I. PROCESSES FOR THE PREPARATION OF ALOE STONE

EXAMPLE 1

Aloe yellow sap was mixed with the antioxidant BHT and one or more acids selected from the group consisting of citric acid, malonic acid, maleic acid, pyruvic acid, and phosphoric acid. The amount of BHT was in the range of 0.001–0.5% w/w based on the whole composition; the weight ratio of the acid to BHT was 0.1 to 10, preferably 1 to 2. The synergistic effect of the selected acid and BHT prevents discoloration when the aloin present in the aloe yellow sap is heated for prolonged periods of time or exposed to sunlight.

EXAMPLE 2

Aloe yellow sap collected from freshly cut aloe leaves was placed in a vat equipped with a stirrer and a heating device. Immediately thereafter, n-propyl gallate in the range of 0.001–0.5% w/w and 0.1% w/w ascorbic acid were added. The entire system was then heated at a temperature of 70° to 85° C. under constant agitation until the solution turned viscous. At that time, the heat was withdrawn and the final mixture was poured into plastic containers. The final aloe stone product possessed a yellow-sanguine color.

A sample of the final product analyzed by HPLC showed a content of 31.8% of aloin isomers A and B. When compared to the 34.8% content of aloin in the sample of aloe yellow sap used, 91.4% of the original amount of aloin was retained [(31.8÷34.8)×100=91.4%].

EXAMPLE 3

A lemon extract, pure lemon juice for example, was mixed with the aloe yellow sap in a 0.25:1 ratio prior to heating. This mixture prevented the discoloration and oxidation of the aloin after the processing of the fresh aloe yellow sap. In one experiment, 50 ml of filtered fresh lemon juice were mixed with 200 ml of fresh aloe yellow sap. The mixture was heated with constant agitation, and once the solution turned highly viscous, it was poured into containers and allowed to solidify. A sample of the final product analyzed by HPLC showed a content of 32.7% of aloin isomers A and B. When compared to the 34.8% content of aloin in the sample of aloe yellow sap used, 94.0% of the original amount of aloin was retained [(32.7÷34.8)×100= 94.0%].

EXAMPLE 4

200 ml of fresh aloe yellow sap were mixed with 0.1% n-propyl-gallate, BHT, or similar antioxidant. Phosphoric acid was added to ensure that the pH of the mixture was between 3 and 5, and then the mixture was heated. The mixture was cooled subsequent to heating, and HPLC analysis revealed an aloin content of 33.6%. When compared to the 34.8% content of aloin in the sample of aloe yellow sap used, this correlates to a 96.6% retention of the original aloin [(33.6÷34.8)×100=96.6%].

II. PROCESSES FOR THE PRODUCTION OF RHEIN AND RHEIN DERIVATIVES

EXAMPLE 5

Figure 4:
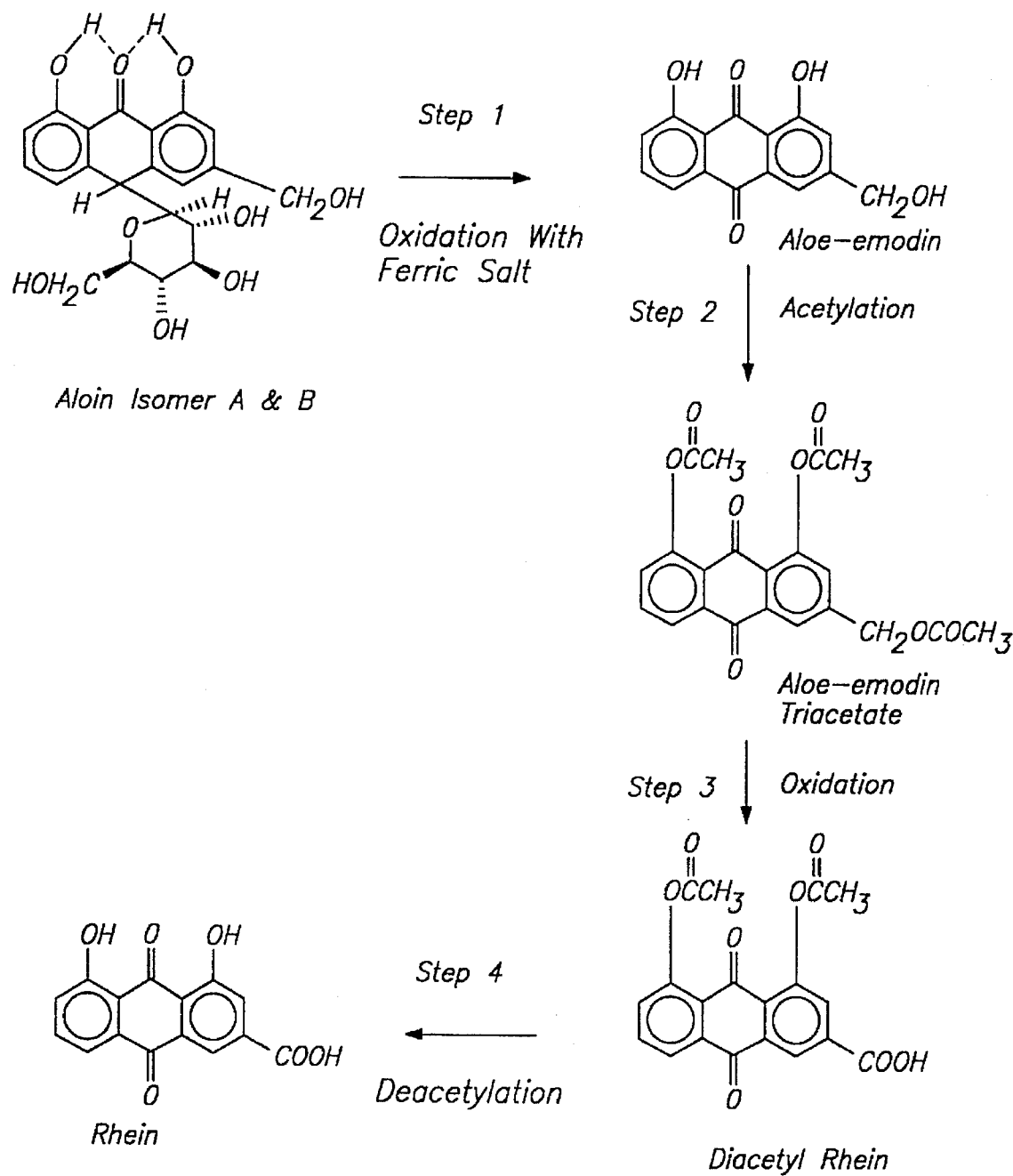
FIG. 4 depicts a chemical scheme for the production of diacetyl rhein and rhein from the starting substrate aloe yellow sap according to the present invention.
Figure 5:
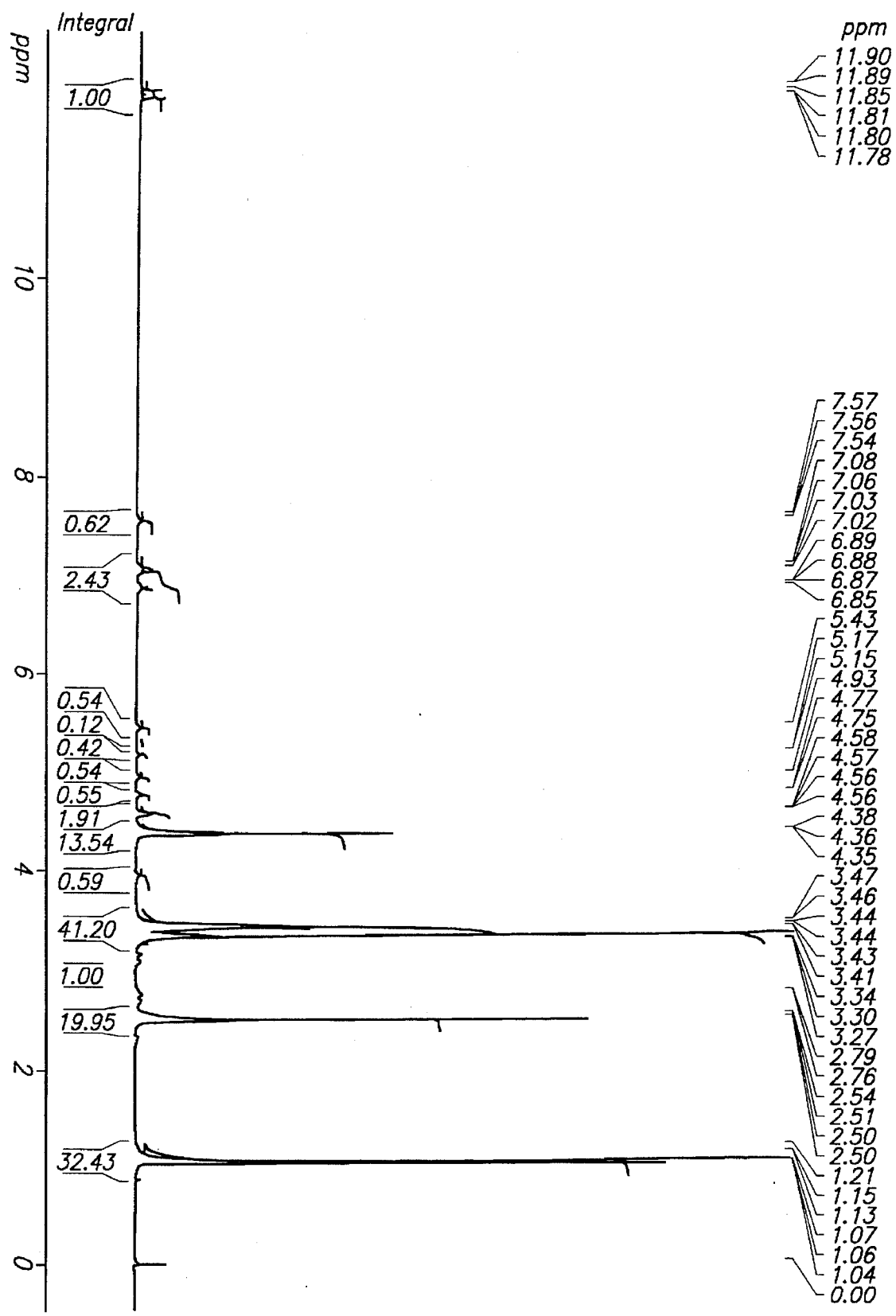
FIG. 5 depicts the 1H, NMR spectra of aloin.
Figure 6:
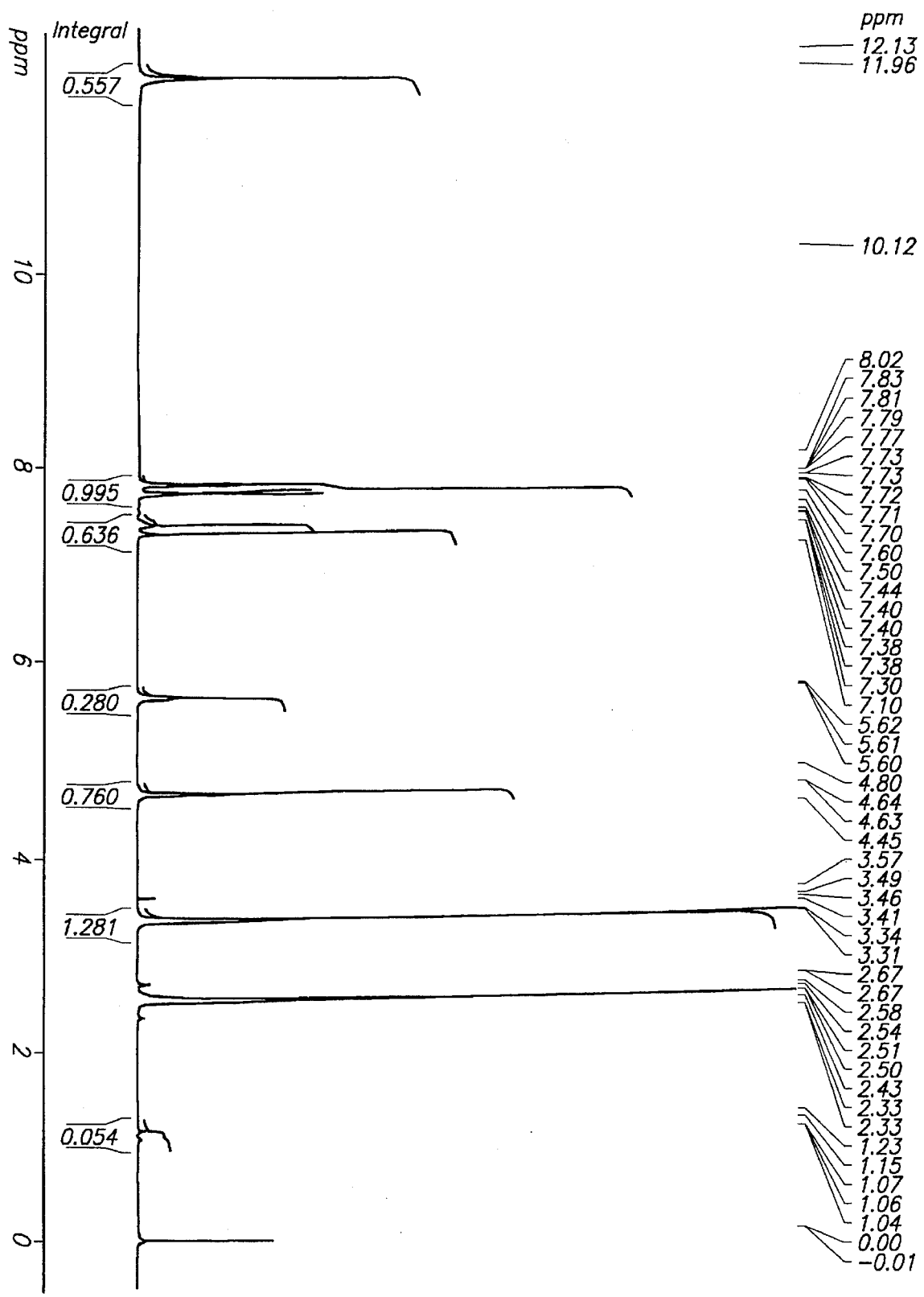
FIG. 6 depicts the 1H, NMR spectra of aloe-emodin.
Figure 7:
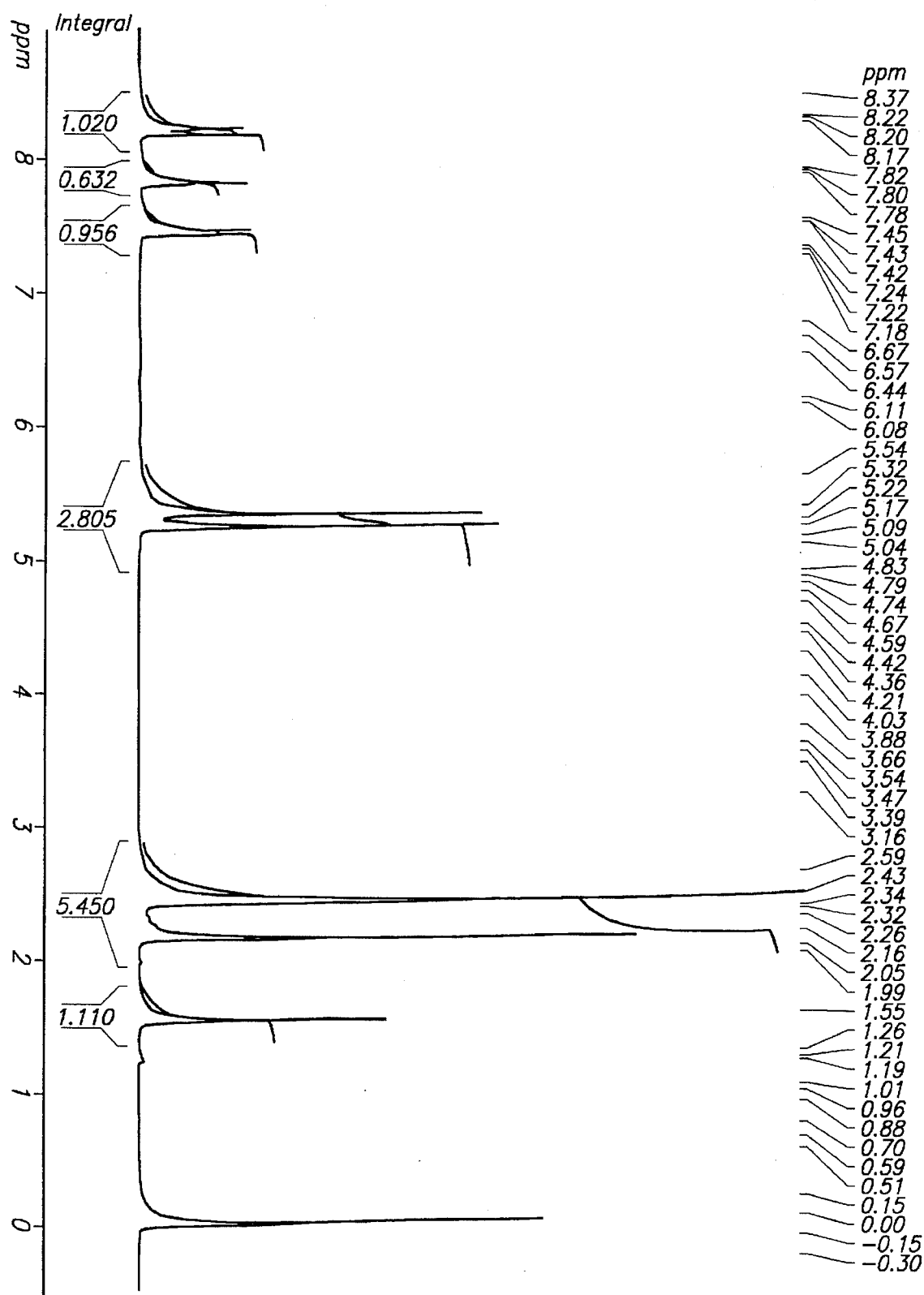
FIG. 7 depicts the 1H, NMR spectra of aloe-emodin triacetate.
Figure 8:
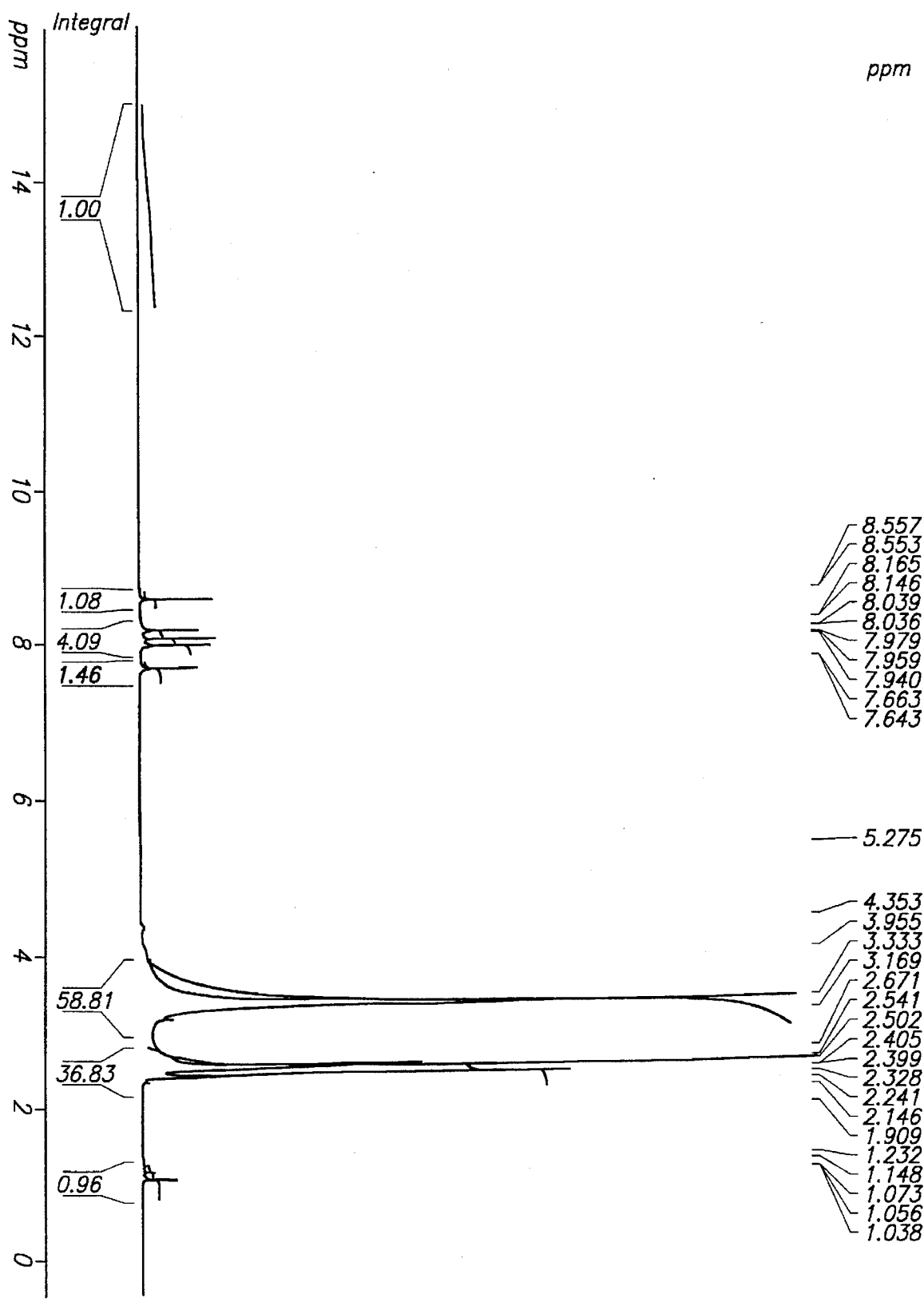
FIG. 8 depicts the 1H, NMR spectra of diacetyl rhein.
Figure 9:
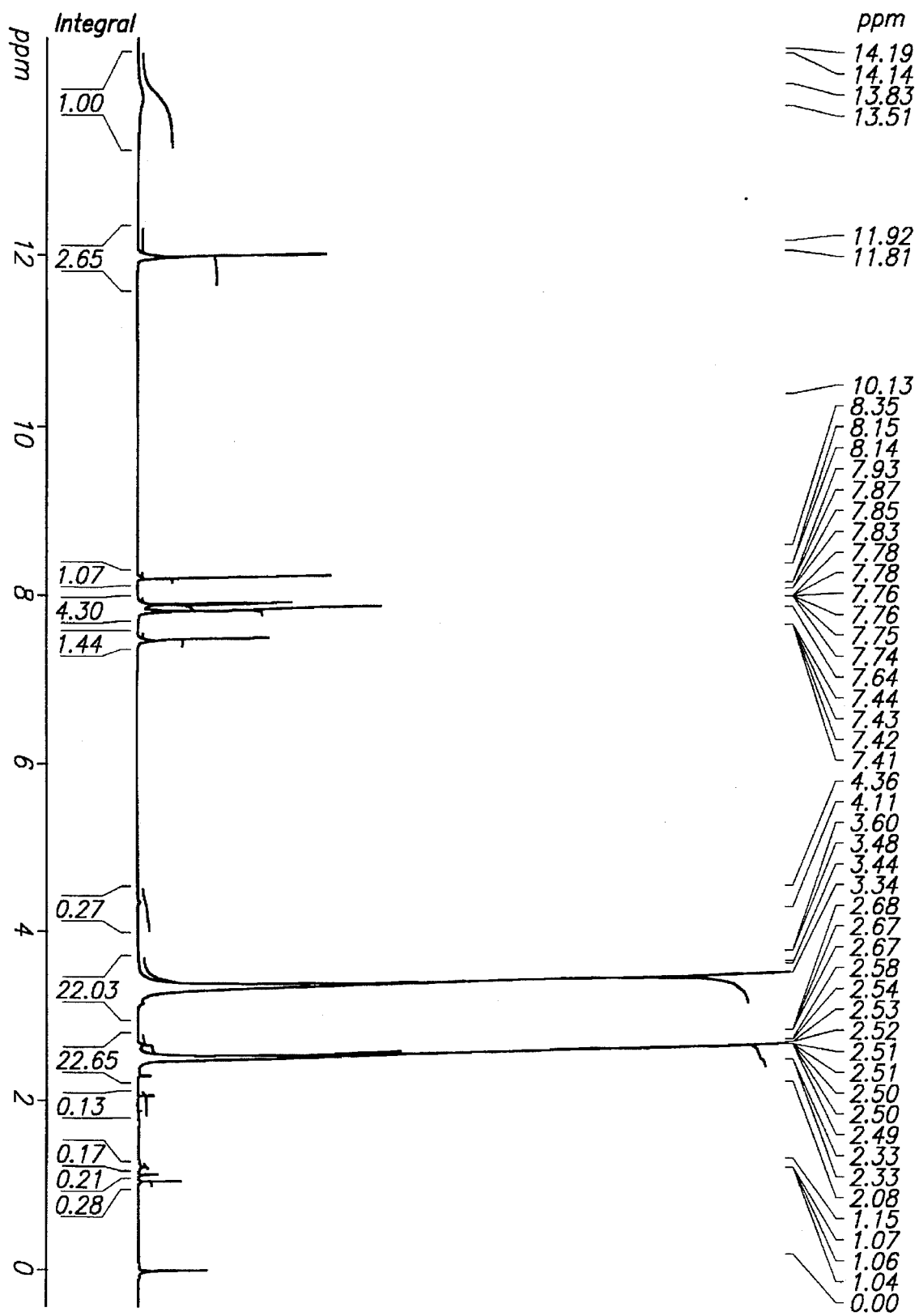
FIG. 9 depicts the 1H, NMR spectra of rhein.

Four-Step Production Of Rhein With A Constant Reflux Procedure In The First Step In order to calculate the overall yield of this first method contemplated by the present invention and to assist in understanding each of the chemical manipulations, the process can be broken down into the following four major parts (FIG. 4): A) Oxidation Of Aloin Contained In Aloe Stone; B) Acetylation Of Aloe-emodin; C) Oxidation of Aloe-emodin Triacetate; and D) Deacetylation of Diacetyl Rhein. Each of these parts will be described in turn.

A. Oxidation Of Aloin Contained In Aloe Stone (1) An acidic solution was prepared by mixing 50 ml of 37% HCl (w/w) solution with 150 ml of deionized water. The acidic solution was then heated at 90° C.

(2) 6.839 g of commercial aloe stone from processed Venezuelan aloe yellow sap were added to the acidic solution with constant agitation. As set forth at the conclusion of part A, 1.926 g of aloin were contained in the 6.839 g sample of commercial aloe stone.

(3) The resulting solution was then brought to boiling for a period of 30 min. Thereafter, the solution was left at room temperature to allow it to cool to room temperature and to ensure sedimentation of the undissolved material present in the aloe stone.

(4) After the solution had achieved room temperature, it was filtered through Whatman No. 90 filter paper, and the filtrate was recollected in a 500 ml flask.

(5) 20 g of $FeCl_3 \cdot 6H_2O$ were then weighed and mixed with 15 ml of deionized water; this mixture, a ferric chloride solution, was agitated until all the material was completely dissolved.

(6) The ferric chloride solution created in step (5) was added to the solution, created in step (4), in the 500 ml flask. The resulting solution was further diluted with 150 ml of demineralized water. A magnetic stirrer was added to the flask, and the flask was coupled with a vertical condenser.

(7) The solution created in step (6) was refluxed for approximately 8 hours. A black solid material was observed at the surface of the solution about 30 min. after initiation of the reflux procedure.

(8) After the approximately 8 hour reflux procedure, the mixture was mixed with approximately 500 ml of cold deionized water and then brought to room temperature by placing it into a cool water bath.

(9) The mixture was then filtered using a Whatman No. 1 filter paper, and the retained black solid material was washed three times with 50 ml of deionized water. All filtrations were done under vacuum in order to extract the majority of the washing water. After the filtrations, the black solid material was placed into a desiccator containing activated silica.

(10) When the black solid material was totally dried, it weighed 2.0 g. 400 ml of toluene were introduced into the flask of the Soxhlet extraction unit. The 2.0 g of black solid material were then deposited into a cellulose extraction thimble and carefully placed into the body of the extractor. The system was then coupled with a condenser and the entire extraction system was placed on a heating plate. The extraction system was heated until the solution coming out from the extraction tube was no longer orange.

(12) Following this approximately 8 hour heating period, the system was brought to room temperature. The extraction system was then dismantled and the toluene solution remaining inside the extractor was mixed with the toluene solution already collected. The resulting hot solution was filtered over a Whatman GFA filter.

(13) The filtered solution was placed into a refrigerator at a temperature of about 5° C. for 1 hour, yielding a good crop of orange-colored crystals. The crystals were then placed in a freezer at a temperature of −10° C. for 2 hours.

(14) The final mass of aloe-emodin crystals was then recovered and filtered over Whatman No. 1 filter paper and washed twice with 5 ml portions of pure toluene. The final crystals were kept in a desiccator containing activated silica under vacuum.

(15) The weight of the completely dried aloe-emodin crystals was found to be 1.098 g. Thereafter, analysis by TLC and HPLC revealed that the aloe-emodin crystals exceeded 95% purity.

The percentage yield of conversion of aloin to aloe-emodin can then be calculated. The amount of pure aloin recoverable from 6.839 g of aloe stone with an aloin content of 28.16% based on HPLC studies is 1.926 g. As the stoichiometry of the reaction is 1:1—one mole of aloin (MW=418.4) yields one mole of aloe-emodin (MW=270.2) —the theoretical yield of pure aloe-emodin from 1.926 g of aloin is 1.244 g: (418.4 g aloin/270.2 g aloe-emodin)=(1.926 g aloin/X g aloe-emodin); X=1.244 g aloe-emodin.

As noted in the final step (Step (15)), supra, 1.098 g of aloe-emodin crystals with purity exceeding 95% were obtained; thus, the product in Step (15) was essentially pure aloe-emodin, which was surprising since it was produced from an aloe stone substrate containing many unwanted oxidized substances. Because 1.244 g was the theoretical yield, the efficiency of the oxidation procedure is 88.3% ((1.098 g obtained÷1.244 g theoretical yield)×100=88.3%).

NMR analysis ($^1$H-NMR; frequency=400 MHz.; solvent= $CD_3OD$) for aloin (FIG. 5) gave the following signals:

12.90 (s, 1H); 11.80 (s, 1H); 7.56 (t, 1H); 6.85–7.08 (m,5H); 5.43 (t, 1H); 5.16 (d, 1H); 4.93 (d, 1H); 4.63 (d, 1H); 4.57 (d,2H); 4.36 (t,2H); 3.27–3.47 (m,4H); 2.51 (m,2H).

NMR analysis ($^1$H-NMR; frequency=400 MHz.; solvent= DMSO-$d_6$) for aloe-emodin (FIG. 6) gave the following signals:

12.13 (s, 1H); 11.96 (s, 1H)); 7.83 (s, 1H); 7.73 (s, 1H); 7.55 (d, 1H); 7.38

(s, 1H); 7.30 (s, 1H); 5.61 (m, 1H); 4.63 (s,2H).

Acetylation Of Aloe-Emodin (1) 3.0 g of aloe-emodin obtained at the conclusion of Part A were placed into a 250 ml Erlenmeyer flask containing 30 ml acetic anhydride and 1 g of sodium acetate. Thus, the desired proportion of aloe-emodin to sodium acetate, the catalyst, is approximately 3:1 (on a gram basis). A magnetic stirrer was placed into the flask and the mixture was heated carefully to avoid reaching temperatures exceeding 90° C.

(2) After 2 hours of heating, the flask was removed and placed at room temperature. Crystallization occurred when the mixture reached ambient temperature.

(3) The final mixture was then poured into approximately 800 ml of cold water and a yellow solid formed, which was then filtered through Whatman No. 42 filter paper. The final solid material was then placed in a desiccator containing activated silica with vacuum.

(4) The resulting solid material had a weight of 4.53 g. The material was then placed in a 125 ml Erlenmeyer flask and 75 ml of toluene were added along with a magnetic stirrer. The contents of the flask were agitated and heated until all of the solid material was solubilized, at which time 0.5 g of activated carbon was added and the solution was heated again for 5 min.

(5) The solution was filtered using Whatman filter No. 1, and the resulting solution was left at room temperature until it reached ambient temperature. After one hour, formation of crystals of aloe-emodin triacetate were observed.

(6) The solution containing the aloe-emodin triacetate crystals was filtered, and the crystals were washed with 5 ml of toluene. The crystals were then placed in a desiccator having activated silica and under reduced pressure. Analysis of the dry crystals by TLC and HPLC revealed a purity exceeding 95%. The weight of the aloe-emodin triacetate crystals was 4.32 g.

The percentage yield of conversion of aloe-emodin to aloe-emodin triacetate was then calculated. The stoichiometry of the reaction is one mole of aloe-emodin (MW=270.2) to one mole of aloe-emodin triacetate (MW=396.3). Both the starting substrate, aloe-emodin, and the final product, aloe-emodin triacetate, had a purity exceeding 95%; thus, no corrections for purity were required to calculate the efficiency of Part B. The 3.0 g of aloe-emodin would provide a theoretical yield of 4.40 g of aloe-emodin triacetate ([270.2 g aloe-emodin/396.3 g aloe-emodin triacetate]=[3.0 g aloe-emodin/X g aloe-emodin triacetate]). Since 4.40 g was the theoretical yield, the efficiency of the acetylation procedure is 98.2% ([4.32 g obtained÷4.40 g theoretical yield]×100).

NMR analysis ($^1$H-NMR; frequency=400 MHz.; solvent= $CDCl_3$) for aloe-emodin triacetate (FIG. 7) gave the following signals:

8.17–8.37 (dd,2H); 7.80 (m, 1H); 7.18–7.24 (dd,2H); 5.20 (d,2H); 2.34 (s,6H); 2.16 (s,3H).

C. Oxidation Of Aloe-Emodin Triacetate (1) 3.0 g of aloe-emodin triacetate crystals were transferred into a 250 ml Erlenmeyer flask.

(2) 30 ml of acetic anhydride and 30 ml of acetic acid were added to the flask, and the solution was then heated at 50° C. until all the aloe-emodin triacetate crystals went into solution.

(3) In a separate 50 ml beaker, 4.5 g of chromium trioxide, 30 ml of acetic acid and 3.0 ml of water were placed. The mixture was agitated until complete dissolution of the chromium trioxide was obtained. The final solution was then transferred into a 25 ml buret.

(4) The solution prepared in Step (2) was then placed into a water bath having a temperature of 27° C. The oxidation procedure was initiated by dropwise addition of the chromium solution created in Step (3); during the oxidation procedure, the water bath temperature must be maintained at 27° or 28° C. for approximately one hour. Thereafter, the water bath temperature was raised to approximately 40° C. for a period of two hours; it is important that the temperature of the water bath not exceed 40° C. during this period.

(5) After the two hour period, the solution was placed at room temperature over night. Subsequently, the solution was poured into a beaker containing about 800 ml of cool deionized water, which formed a fine greenish-yellow colored solid suspended in the solution. This solid was filtered and washed three times with approximately 50 ml portions of cool water. The resulting solid, containing diacetyl rhein, was placed into a desiccator containing activated silica and dried under reduced pressure.

(6) The diacetyl rhein was then analyzed by TLC and HPLC, revealing a purity exceeding 95%. The diacetyl rhein's final weight was 2.61 g. The percentage yield of conversion of aloe-emodin triacetate to diacetyl rhein was then calculated. The stoichiometry of the reaction is one mole of aloe-emodin triacetate (MW=396.3) to one mole of diacetyl rhein (MW=368.3). Both the starting substrate, aloe-emodin triacetate, and the final product, diacetyl rhein, had a purity exceeding 95%; thus, no corrections for purity were required to calculate the efficiency of Part C. The theoretical yield of pure diacetyl rhein from 3.0 g of pure aloe-emodin triacetate is 2.79 g ([396.3 g aloe-emodin triacetate/368.3 g diacetyl rhein]=[3.0 g aloe-emodin triacetate/X g diacetyl rhein]). Since 2.79 g was the theoretical yield, the efficiency of the oxidation procedure is 93.5% ([2.61 g obtained÷2.79 g theoretical yield]×100).

NMR analysis ($^1$H-NMR; frequency=400 MHz.; solvent= DMSO-$d_6$) for diacetyl rhein (FIG. 8) gave the following signals:

8.56 (d, 1H); 7.94–8.16 (dd,3H); 7.65 (d, 1H); 3.95 (s,2H); 2.33 (s,6H).

D. Deacetylation of Diacetyl Rhein (1) 3.0 g of diacetyl rhein, 25 ml of methanol and a magnetic stirrer were placed in a 250 ml Erlenmeyer flask.

(2) The system was agitated and 25 ml of water and 3.0 g of KOH were then added. The resulting mixture was heated at 65° C. for approximately 30 min.

(3) After the first heating period, 20 ml of 6 N HCl solution were added, increasing the solution's viscosity; the 6 N HCl solution functions to both neutralize the excess KOH and to neutralize the potassium salt of rhein. 20 ml of water were then added, and the final solution was heated to boiling for about 30 min. in order to assure that all of the acetyl groups have been removed.

(4) After cooling, the solution was filtered using Whatman filter No. 1. The retained solid was washed three times with 20 ml portions of water, and the final solid was placed in a desiccator containing activated silica and dried under reduced pressure.

(5) The final weight of the solid was 2.77 g. The solid material was transferred into a 50 ml beaker and 20 ml of DMSO and 300 mg of activated carbon were added. This mixture was heated for 10 min. at 80° C. The solution was filtered over a Whatman filter paper No. 42 and the final solution was left at ambient temperature.

(6) Rhein crystals were formed during cooling of the solution. Analysis of the crystals by TLC and HPLC revealed a final purity exceeding 95%. The final weight of the rhein crystals was 2.24 g.

The percentage yield of conversion of diacetyl rhein to rhein was then calculated. The stoichiometry of the reaction is one mole of diacetyl rhein (MW=368.3) to one mole of rhein (MW=284.2). Both the starting substrate, diacetyl rhein, and the final product, rhein, had a purity exceeding 95%; thus, no corrections for purity were required to calculate the efficiency of Part D. The theoretical yield of pure rhein from 3.0 g of pure diacetyl rhein is 2.31 g ([368.3 g diacetyl rhein/284.2 g rhein]=[3.0 g diacetyl rhein/X g rhein]). Since 2.31 g was the theoretical yield, the efficiency of the oxidation procedure is 97.0% ([2.24 g obtained÷2.31 g theoretical yield]×100).

NMR analysis ($^1$H-NMR; frequency=400 MHz.; solvent= DMSO-$d_6$) for rhein (FIG. 9) gave the following signals:

14.14 (bs, 1H); 11.92 (s, 1H); 11.81 (s, 1H); 8.35 (s, 1H); 7.64–7.93 (dt,3H); 7.43 (d, 1H).

The overall efficiency of the first process contemplated by the invention, expressed as a percentage, is calculated as follows: % efficiency of the process=(% efficiency of Part A)×(% efficiency of Part B)×(% efficiency of Part C)×(% efficiency of Part D)×100. Thus, the overall % efficiency= (88.3/100)×(98.2/100)×(93.5/100)×(97.0/100)×100=78.6%.

EXAMPLE 6

Four-Step Production Of Rhein Wherein The First Oxidation Step Is Driven By Ultraviolet Irradiation And Followed By A Final Reflux of Four Hours As was the case in Example 5, supra, this process of the present invention can be broken down into the following four major parts (FIG. 4): A) Oxidation Of Aloin Contained In Aloe Stone; B) Acetylation Of Aloe-emodin; C) Oxidation of Aloe-emodin Triacetate; and D) Deacetylation of Diacetyl Rhein. However, as Parts B) through D) are analogous to those parts in Example 5, they will not be set forth again.

A. Oxidation Of Aloin Contained In Aloe Stone

Steps (1) through (6) from Part A in Example 5 also apply here. At the completion of Step (6), the solution was left at room ambient temperature in direct sunlight for approximately one week to drive the oxidation reaction. After five to eight days, the solution was refluxed for approximately 4 hours to ensure the oxidation reaction went to completion. The final solution was then treated as presented in Steps (8) through (15) from Example 5.

Again, TLC and HPLC analysis revealed that the purity of the aloe-emodin crystals exceeded 95%; the final weight of the completely dried aloe-emodin crystals was found to be 1.010 g. The 1.244 g theoretical yield derived in Example 5 is still applicable because the same amount of starting substrate was used in Example 6. Therefore, this alternative oxidation process has an efficiency of 81.2% ([1.010 g obtained÷1.244 g theoretical yield]×100).

The overall efficiency of the second process of the present invention can then be calculated using the percentage yields for Parts B) through D) from Example 5. Percentage efficiency of the process=(% efficiency of Part A)×(% efficiency of Part B)×(% efficiency of Part C)×(% efficiency of Part D)×100. The overall percentage efficiency thus=(81.2/100) ×(98.2/100)×(93.5/100)×(97.0/100)×100=72.3%.

The benefit of this oxidation technique is clear. As soon as the leaves are cut from the mother plant, the aloe yellow sap can be collected and combined with the mixture of ferric chloride and HCl solutions. This combination can then be left under direct sunlight in the fields containing the aloe plants for the requisite five to eight days. There is no need to first remove the aloe yellow sap to a separate processing area.

EXAMPLE 7

Two-Step Production Of Rhein

Both of the aforementioned processes entailed four primary chemical steps. The rationale for using a four-step process, as opposed to a process with fewer steps, is that each of the intermediate compounds formed in the four-step processes shows promising biological activity. Specifically, the inventors have determined that aloe-emodin, aloe-emodin triacetate, and diacetyl rhein all have shown biological activity against mycobacteria. However, the need to isolate and purify these intermediate compounds will likely decrease the efficiency and increase the cost of producing the final rhein product. As a result, a more direct chemical scheme is now proposed. In order to understand the steps of this third process of the present invention and to assist in calculating its overall yield, the process can be broken down into the following two major parts: A) Oxidation of Aloin Contained in Aloe Stone; B) Production of Rhein from Aloe-emodin.

A. Oxidation Of Aloin Contained In Aloe Stone

The production of aloe-emodin from aloe stone may be performed by either of the two methods presented in Examples 5 and 6. However, the overall yield of rhein will obviously depend on which process is chosen.

B. Production Of Rhein From Aloe-Emodin (1) 2.0 g of aloe-emodin obtained in Part A were placed in a 250 ml Erlenmeyer flask. 40 ml of acetic anhydride and 1 drop of concentrated $H_2SO_4$ (approximately 50 mg) were added to the flask. Thus, the desired proportion of aloe-emodin to $H_2SO_4$, the catalyst, is approximately 40:1 (on a gram basis). A magnetic stirring bar was placed into the flask, and the flask was then heated in a water bath at 80° C. under constant agitation.

(2) The dissolution of aloe-emodin occurred gradually due to its chemical nature. After going into solution, the aloe-emodin began reacting because of the presence of the acid catalyst. After approximately 30 min., all of the aloe-emodin had dissolved and the reaction mixture changed from an orange-red color to an orange-yellow color.

(3) The flask was heated for a total time of approximately 1 hour. Thereafter, the reaction mixture was cooled in a water bath at about 15° C. and an additional 15 ml of acetic anhydride were added to the reaction mixture.

(4) An oxidation solution comprised of 5.0 g of chromic acid, 25 ml of acetic acid, and 1.5 ml of water was created. This solution was added dropwise over approximately a 60 min. period to the cooled reaction mixture. After the initial 45 min. of the 60 min. period, the presence of a solid in the reacting mixture was observed. Following the full approximately 60 min. period, the final reaction mixture was heated at 45° C. for approximately two hours. The final reaction mixture was then placed at room temperature for a period of approximately two hours in order to allow the resulting solid particles to precipitate. A solid mass was then obtained by decantation.

(5) In order to hydrolyze all the acetic anhydride, the solid mass was then suspended in 1 liter of water at 0° C. and mixed constantly for 1 hour.

(6) The solid mass was next separated by filtration under vacuum and washed three times with 50 ml of water.

(7) The resulting solid material was then placed in an Erlenmeyer flask along with 25 ml of methanol and a magnetic stirring bar. The flask was agitated and 25 ml of water and 3 g of KOH were added. This mixture was heated at approximately 65° C. for approximately 30 min.

(8) After the first heating period, 20 ml of 6 N HCl solution were added, increasing the solution's viscosity; the 6 N HCl solution functions to both neutralize the excess KOH and to neutralize the potassium salt of rhein. 20 ml of water were then added, and the resulting solution was heated to boiling for a period of approximately 30 min.

(9) After the final heating period, this solution was left at room temperature. Upon achieving room temperature, it was filtered using Whatman filter paper No. 1.

(10) The retained solid material was washed three times with 20 ml portions of water. Thereafter, the solid material was placed in a desiccator containing activated silica and dried under reduced pressure. The dried solid weighed 1.89 g.

(11) The dried solid material was crystallized in order to remove impurities present therein. The solid material was transferred into a 50 ml beaker and 20 ml of DMSO were added along with 300 mg of powdered activated carbon. The beaker was then heated for approximately 10 min. at approximately 80° C., after which the solution was filtered using Whatman filter No. 42.

(12) The filtrate was left at room temperature to cool. Upon cooling, rhein crystals in the form of orange needles were formed. TLC and HPLC analysis of the rhein revealed a purity exceeding 95%, and its final weight was 1.71 g.

The percentage yield of conversion of aloe-emodin to rhein was then calculated. The stoichiometry of the reaction is one mole of aloe-emodin (MW=270.2) to one mole of rhein (MW=284.2). Both the starting substrate, aloe-emodin, and the final product, rhein, had a purity exceeding 95%; thus, no corrections for purity were required to calculate the efficiency. The theoretical yield of pure rhein from 2.0 g of pure aloe-emodin is 2.1 g ([270.2 g aloe emodin/284.2 g rhein]=[2.0 g aloe-emodin/X g rhein]). Since 2.1 g was the theoretical yield, the efficiency of the procedure is 81.4% ([1.71 g obtained÷2.1 g theoretical yield]×100).

The overall efficiency of this process of the present invention, expressed as a percentage, is calculated as follows: % efficiency of the process=(% efficiency of Part A)×(% efficiency of Part B)×100. If the percentage yield of conversion of aloin to aloe yellow sap obtained in Example 5 is used for Part A, the overall % efficiency=(88.3/100)× (81.4/100)×100 =71.9%.

EXAMPLE 8

Two-Step Production Of Diacetyl Rhein

As diacetyl rhein has also shown promise as a therapeutic agent, an abbreviated process for its production is now presented. Similar to Example 7, this process of the present invention can best be understood if it is broken down into the following two major parts: A) Oxidation of Aloin Contained in Aloe Stone; B) Production of Diacetyl Rhein from Aloe-emodin.

A. Oxidation Of Aloin Contained In Aloe Stone

The production of aloe-emodin from aloe stone may be performed by either of the two methods presented in Examples 5 and 6. However, the overall yield of diacetyl rhein will obviously depend on which process is chosen.

B. Production Of Diacetyl Rhein From Aloe-Emodin

Steps (1) through (6) from Example 7, Part B, also apply here. At the completion of Step (6), the solid was dried in a desiccator under vacuum. TLC and HPLC analysis of the diacetyl rhein revealed a purity exceeding 95%, and its final weight was 2.42 g.

The percentage yield of conversion of aloe-emodin to diacetyl rhein was then calculated. The stoichiometry of the reaction is one mole of aloe-emodin (MW=270.2) to one mole of diacetyl rhein (MW=368.3). Both the starting substrate, diacetyl rhein, and the final product, rhein, had a purity exceeding 95%; thus, no corrections for purity were required to calculate the efficiency. The theoretical yield of pure diacetyl rhein from 2.0 g of pure aloe-emodin is 2.73 g ([270.2 g aloe emodin/368.3 g diacetyl rhein]=[2.0 g aloe-emodin/X g diacetyl rhein]). Since 2.73 g was the theoretical yield, the efficiency of the procedure is 88.6% ([2.42 g obtained÷2.73 g theoretical yield]×100).

EXAMPLE 9

Production Of Aloe-Emodin From Aloe Stone Using Ferric Sulfate

This example describes the oxidation of aloin contained in a sample of aloe stone to produce aloe-emodin. Thus, this example provides an alternative to the methods set forth in Part A of Examples 5 and 6, supra, for forming aloe-emodin. Following the formation of aloe-emodin, rhein or diacetyl rhein can be produced therefrom by using either the method provided in Example 5, Parts B through D, or the abbreviated methods provided in Examples 7 and 8, Part B.

(1) An acidic solution was prepared by mixing 33.6 ml of concentrated sulfuric acid (95% w/w; density of 1.84) with 170 ml of deionized water (the acidic solution created was approximately 6 N). The acidic solution was then heated at 90° C.

(2) 6.801 g of commercial aloe stone (prepared by using aloe yellow sap of *Aloe barbadensis miller* plants grown in Venezuela) were added to the acidic solution under constant agitation. As set forth at the conclusion of this example, 1.915 g of aloin were contained in the 6.801 g sample of commercial aloe stone.

(3) The resulting solution was then brought to boiling for a period of 30 min. Thereafter, the solution was left at room temperature to allow it to cool to room temperature and to ensure sedimentation of the undissolved material present in the aloe stone.

(4) After the solution had achieved room temperature, it was filtered through Whatman No. 90 filter paper, and the filtrate was recollected in a 500 ml Erlenmeyer flask.

(5) 19 g of $Fe_2(SO_4)_3 \cdot 5H_2O$ containing about 22% iron were weighed and mixed with 20 ml of deionized water; this mixture, a ferric sulfate solution, was agitated until all the material was completely dissolved.

(6) The ferric sulfate solution created in step (5) was added to the solution, created in step (4), in the 500 ml Erlenmeyer flask. The mouth of the flask was plugged with a piece of glass wool.

(7) The reaction mixture created in step (6) was then placed inside an autoclave equipped with a temperature and a pressure sensor gauge. The system was then brought to a temperature of 121° C. and a pressure of 15 psi for a duration of 2 hours. Following the two-hour period, the autoclave was cooled to room temperature and the Erlenmeyer flask was removed.

(8) The contents of the Erlenmeyer flask were then mixed with 500 ml of deionized water. The mixture was then filtered using a Whatman No. 1 filter paper, and the retained black solid material was washed three times with 50 ml of deionized water. All filtrations were done under vacuum in order to extract the majority of the washing water. After the filtrations, the black solid material was placed into a desiccator containing activated silica.

(9) 400 ml of toluene were introduced into the flask of a Soxhlet extraction unit. The black solid material was then deposited into a cellulose extraction thimble and carefully placed into the body of the extractor. The system was then coupled with a condenser and the entire extraction system was placed on a heating plate. The extraction system was heated until the solution coming out from the extraction tube was no longer orange.

(10) Following this approximately 8 hour heating period, the system was brought to room temperature. The extraction system was then dismantled and the toluene solution remaining inside the extractor was mixed with the toluene solution already collected. The resulting hot solution was filtered over a Whatman GFA filter.

(11) The filtered solution was placed into a refrigerator at a temperature of about 5° C. for 1 hour, yielding a good crop of orange-colored crystals. The crystals were then placed in a freezer at a temperature of −10° C. for 2 hours.

(12) The final mass of aloe-emodin crystals was then recovered and filtered over Whatman No. 1 filter paper and washed twice with 5 ml portions of pure toluene. The final crystals were kept in a desiccator containing activated silica under vacuum.

(13) The weight of the completely dried aloe-emodin crystals was found to be 1.120 g. Thereafter, analysis by TLC and HPLC revealed that the aloe-emodin crystals exceeded 95% purity.

The percentage yield of conversion of aloin to aloe-emodin can then be calculated. The amount of pure aloin recoverable from 6.801 g of aloe stone with an aloin content of 28.16% based on HPLC studies is 1.915 g. As the stoichiometry of the reaction is 1:1—one mole of aloin (MW=418.4) yields one mole of aloe-emodin (MW=270.2) —the theoretical yield of pure aloe-emodin from 1.915 g of aloin is 1.237 g: (418.4 g aloin/270.2 g aloe-emodin)=(1.915 g aloin/X g aloe-emodin); X =1.237 g aloe-emodin.

Because 1.237 g was the theoretical yield, the efficiency of the oxidation procedure is 90.5% ((1.120 g obtained÷1.237 g theoretical yield)×100=90.5%). Thus, oxidation with ferric sulfate resulted in an efficiency about 2.2% above the 88.3% obtained in Example 5 using ferric chloride. This small increase would likely be significant with large-scale production of aloe-emodin.

III. OTHER EXAMPLES

EXAMPLE 10

Production of Rhein From The Leaves of *Kniphofia foliosa*

Part A in preceding Examples 5 through 8 involved the transformation of aloin into aloe-emodin. However, this transformation step can be avoided if aloe-emodin itself can be obtained from a plant source. The leaves of *Kniphofia foliosa* contain aloe-emodin acetate.

An acetone extract of the leaves of *Kniphofia foliosa* was prepared. The solvent was then removed, yielding an aloe-emodin acetate-enriched solid material. After drying, the resulting solid material was extracted with toluene using a Soxhlet extraction unit, and then the solvent was removed yielding a final solid residue. This final solid residue was subsequently treated according to steps (1) through (12) from Example 7, Part B, producing rhein as the final product. A yield of about 90% was obtained using this process of the present invention.

EXAMPLE 11

Comparison of The Ratios of Reactants Employed in Ferric Salt Oxidation

As previously indicated, the ratio of ferric salt to aloin employed in the present invention differs from that utilized in the past. This Example numerically illustrates the differences.

A. British and European Pharmacopoeias

The description of the assay of aloes presented in the British and European Pharmacopoeias indicates that 2 mg of Curacao aloe paste (contained in 10 ml of the sample solution of 0.2 g of commercial aloe stone dissolved in 1 liter solution) reacts with 1 ml of a 60% (w/v) ferric chloride solution.

The amount of aloin within such aloe paste must first be determined. The British Pharmacopoeia indicates that Curacao aloes contain at least 30% of anhydrous barbaloin, or aloin. Thus, 0.6 mg of aloin will be present in 2 mg of Curacao aloe paste (2 mg (30%)=0.6 mg aloin). 1 ml of the 60% (w/v) ferric chloride solution contains 0.6 g of ferric chloride. Therefore, the gram-to-gram ratio of aloin to ferric chloride is about 1:1000.

B. The Present Invention: Ferric Chloride

As set forth in Example 5, supra, 1.926 g of aloin were contained in the 6.839 g sample of commercial aloe stone (based on HPLC studies). Thus, about 1.93 g aloin were combined with 20 g of ferric chloride. Therefore, the gram-to-gram ratio of aloin to ferric chloride is about 1:10.

The proportion of iron to ferric chloride used in Example 5, expressed as a percentage on a gram basis, can be calculated as follows:

=(MW of iron÷MW of $FeCl_3·6H_2O$)×100
=(55.8÷270.3)×100
=20.6%

For ferric chloride oxidation, the content of the ferric ion in the ferric chloride is inherently defined by the molecular formula of ferric chloride.

C. The Present Invention: Ferric Sulfate

As set forth in Example 9, supra, 1.915 g of aloin were contained in the 6.801 g sample of commercial aloe stone (based on HPLC studies). Thus, about 1.91 g aloin were combined with 19 g of ferric sulfate. Therefore, the gram-to-gram ratio of aloin to ferric sulfate is about 1:10.

The proportion of iron to ferric sulfate used in Example 9, expressed as a percentage on a gram basis, can be calculated as follows:

=(MW of iron÷MW of $Fe_2(SO_4)_3·5H_2O$)×100
=(111.6÷489.9)×100
=22.8%

For ferric sulfate oxidation, the content of the ferric ion in the ferric sulfate must be specified by the manufacturing chemist, as ferric sulfate does not have a defined molecular formula from which the content may be calculated. By way of example, if one only has access to ferric sulfate containing 15% ferric ions, then a larger amount of ferric sulfate will need to be used in order to keep the ratio of aloin to ferric sulfate at about 1:10.

From the above, it should be evident that the present invention provides for the production of rhein and rhein derivatives by methods that are more efficient and economical than those used previously. These methods are clearly needed to fulfill the larger demand for rhein that is almost certain to develop in the future.

We claim:

1. A method of producing rhein from aloin-containing substances comprising the steps of:
   (a) providing a substance containing aloin;
   (b) oxidizing said aloin to produce aloe-emodin wherein said oxidizing comprises using a ferric salt solution; and
   (c) treating said aloe-emodin to produce rhein.
2. The method of claim 1 wherein said aloin-containing substance is a plant exudate.

3. The method of claim 2 wherein said plant exudate is aloe yellow sap.

4. The method of claim 3 wherein said aloe yellow sap is obtained from *Aloe barbadensis miller.*

5. The method of claim 1 wherein said oxidizing step has an efficiency of greater than approximately 70%.

6. The method of claim 1 wherein said oxidizing of aloin further comprises the steps of:
  (a) adding said aloin to a solution comprising an acid catalyst to create a first reaction mixture;
  (b) reacting said first reaction mixture to produce a dissolution mixture comprising a liquid and a sediment;
  (c) separating said liquid from said sediment by filtering said dissolution mixture to produce a filtrate;
  (d) adding said ferric salt solution and a diluent to said filtrate to create a second reaction mixture;
  (e) reacting said second reaction mixture to produce a reaction product; and
  (f) extracting aloe-emodin from said reaction product.

7. The method of claim 6 wherein said acid catalyst is a hydrochloric acid solution and said ferric salt solution consists essentially of ferric chloride.

8. The method of claim 7 wherein said reacting said second reaction mixture comprises refluxing said second reaction mixture.

9. The method of claim 7 wherein said reacting said second reaction mixture occurs in the presence of ultraviolet irradiation.

10. The method of claim 9 wherein said reacting said second reaction mixture further comprises leaving said second reaction mixture at room temperature under direct sunlight exposure for a period of time ranging from 5 to 8 days.

11. The method of claim 6 wherein said acid catalyst is a sulfuric acid solution and said ferric salt solution consists essentially of ferric sulfate.

12. The method of claim 11 wherein said reacting said second reaction mixture comprises subjecting said second reaction mixture to a temperature of approximately 121° C. and a pressure of approximately 15 psi.

13. The method of claim 6 wherein said ferric salt solution contains a ferric salt having a proportion, on a gram basis, of ferric ion to said ferric salt of between approximately 21 and 23%.

14. The method of claim 6 wherein said extracting of aloe-emodin comprises adding toluene to said reaction product.

15. The method of claim 1 wherein said treating comprises the steps of:
  (a) acetylating said aloe-emodin to produce aloe-emodin triacetate;
  (b) oxidizing said aloe-emodin triacetate to produce diacetyl rhein; and
  (c) deacetylating said diacetyl rhein to produce rhein.

16. The method of claim 15 wherein said acetylating of aloe-emodin comprises the steps of:
  (a) combining aloe-emodin with an acetylating agent and a catalyst to form a reaction mixture;
  (b) reacting said reaction mixture to produce a reaction product; and
  (c) isolating aloe-emodin triacetate from said reaction product.

17. The method of claim 16 wherein said catalyst is sodium acetate, said aloe-emodin being combined with said sodium acetate on a gram-to-gram ratio of approximately 3:1.

18. The method of claim 16 wherein said catalyst is sulfuric acid, said aloe-emodin being combined with said sulfuric acid on a gram-to-gram ratio of approximately 40:1.

19. The method of claim 15 wherein said deacetylating of diacetyl rhein comprises the steps of:
  (a) agitating a mixture comprising diacetyl rhein and an alcohol to form a first solution;
  (b) adding a deacetylating agent to said first solution to form a second solution;
  (c) reacting said second solution to form a final solution; and
  (d) isolating rhein from said final solution.

20. The method of claim 19 wherein said deacetylating agent comprises potassium hydroxide.

21. A method of producing rhein from aloin-containing substances comprising the steps of:
  (a) providing aloe stone containing at least approximately 20% aloin by weight;
  (b) oxidizing said aloin to produce aloe-emodin wherein said oxidizing comprises using a ratio, on a gram basis, of said aloin to a ferric salt of between approximately 1:7 and 1:11; and
  (c) treating said aloe-emodin to produce rhein wherein said treating comprises:
    (i) acetylating said aloe-emodin to produce aloe-emodin triacetate;
    (ii) oxidizing said aloe-emodin triacetate to produce diacetyl rhein; and
    (iii) deacetylating said diacetyl rhein to produce rhein.

22. The method of claim 21 wherein said aloin-containing substance is a plant exudate.

23. The method of claim 22 wherein said plant exudate is aloe yellow sap.

24. The method of claim 23 wherein said aloe yellow sap is obtained from *Aloe barbadensis miller.*

25. The method of claim 21 wherein said ferric salt is ferric chloride.

26. The method of claim 21 wherein said ferric salt is ferric sulfate.

27. A method of treating a mycobacterial infection caused by mycobacteria from the group consisting of *Mycobacterium tuberculosis, M. avium,* and *M. paratuberculosis* comprising orally administering an effective amount of a therapeutic composition comprising a purified anthraquinone derivative to a host suspected of suffering from said mycobacterial infection.

28. The method of claim 27 wherein said purified anthraquinone derivative is selected from the group consisting of rhein, diacetyl rhein, and aloe-emodin triacetate.

29. The method of claim 27 wherein said host is selected from the group consisting of humans and animals.

30. The method of claim 29 wherein said animal is selected from the group consisting of ruminants, fowl, and swine.

31. A method of treating a mycobacterial infection comprising administering to a host suspected of suffering from said mycobacterial infection an effective amount of a therapeutic composition comprising a purified anthraquinone derivative selected from the group consisting of rhein, diacetyl rhein, and aloe-emodin triacetate.

32. The method of claim 31 wherein said mycobacterial infection is caused by mycobacteria from the group consisting of *Mycobacterium tuberculosis, M. avium,* and *M. paratuberculosis.*

33. The method of claim 32 wherein said host is selected from the group consisting of humans and animals.

34. The method of claim 33 wherein said animal is selected from the group consisting of ruminants, fowl, and swine.

* * * * *

UNITED STATES PATENT AND TRADEMARK OFFICE
CERTIFICATE OF CORRECTION

PATENT NO. : 5,652,265
DATED : July 29, 1997
INVENTOR(S) : Natale Vittori et al.

It is certified that error appears in the above-indentified patent and that said Letters Patent is hereby corrected as shown below:

In col. 2, line 17, "Rheim" should be replaced with --Rhein:--

In col. 2, line 53, "Quire." should be replaced with --Quirm.--

In col. 3, line 28, "eraodin" should be replaced with --emodin--

In col. 4, line 20, "sermosides" should be replaced with --sennosides--

In col. 12, line 42, "290 ng/µl x 20" should be replaced with --290 ng/µl x 20 µl--

In col. 12, line 46, "area+slope" should be replaced with --area÷slope--

In col. 12, line 47, "21.08+0.0235" should be replaced with --21.08÷0.0235--

In col. 12, line 50, "A+total" should be replaced with --A÷total--

In col. 12, line 52, "µg+5.8" should be replaced with --µg÷5.8--

In col. 12, line 56, "area+slope" should be replaced with --area÷slope--

In col. 12, line 57, "21.37+0.0235" should be replaced with --21.37÷0.0235--

UNITED STATES PATENT AND TRADEMARK OFFICE
CERTIFICATE OF CORRECTION

PATENT NO. : 5,652,265
DATED : July 29, 1997
INVENTOR(S) : Natale Vittori et al.

It is certified that error appears in the above-indentified patent and that said Letters Patent is hereby corrected as shown below:

In col. 12, line 60, "B+total" should be replaced with --B÷total--

In col. 12, line 62, "µg+5.8" should be replaced with --µg÷5.8--

In col. 14, line 14, "28.2+34.8" should be replaced with --28.2÷34.8--

In col. 24, line 22, "obtained 2.79" should be replaced with --obtained ÷ 2.79--

Signed and Sealed this

Thirtieth Day of December, 1997

Attest:

BRUCE LEHMAN

Attesting Officer

Commissioner of Patents and Trademarks